US011306352B2

(12) United States Patent
Morley

(10) Patent No.: US 11,306,352 B2
(45) Date of Patent: Apr. 19, 2022

(54) NUCLEIC ACID AMPLIFICATION METHOD AND PRIMERS FOR USE THEREIN

(71) Applicant: Monoquant Pty Ltd., Adelaide (AU)

(72) Inventor: Alexander Alan Morley, Toorak (AU)

(73) Assignee: Monoquant Pty Ltd., Adelaide (AU)

( * ) Notice: Subject to any disclaimer, the term of this patent is extended or adjusted under 35 U.S.C. 154(b) by 0 days.

(21) Appl. No.: 16/478,786

(22) PCT Filed: Jun. 7, 2019

(86) PCT No.: PCT/AU2019/050591
§ 371 (c)(1),
(2) Date: Jul. 17, 2019

(87) PCT Pub. No.: WO2019/237146
PCT Pub. Date: Dec. 19, 2019

(65) Prior Publication Data
US 2021/0087619 A1 Mar. 25, 2021

Related U.S. Application Data

(60) Provisional application No. 62/757,634, filed on Nov. 8, 2018, provisional application No. 62/683,415, filed on Jun. 11, 2018.

(51) Int. Cl.
*C12P 19/34* (2006.01)
*C12Q 1/6858* (2018.01)
*C12Q 1/6881* (2018.01)
*C12Q 1/6886* (2018.01)

(52) U.S. Cl.
CPC ......... *C12Q 1/6858* (2013.01); *C12Q 1/6881* (2013.01); *C12Q 1/6886* (2013.01); *C12Q 2600/156* (2013.01); *C12Q 2600/158* (2013.01)

(58) Field of Classification Search
CPC .......................... C12Q 1/6858; C12Q 1/6881
See application file for complete search history.

(56) References Cited

U.S. PATENT DOCUMENTS

| 2009/0209432 A1* | 8/2009 | Morley | C07H 21/04 |
| | | | 506/9 |
| 2014/0017685 A1* | 1/2014 | Fu | C12Q 1/6853 |
| | | | 435/6.11 |
| 2018/0208984 A1* | 7/2018 | Looney | C12Q 1/6876 |

OTHER PUBLICATIONS

Liu et al., BMC Biotechnology 13(21), 1-8 (2013). (Year: 2013).*

* cited by examiner

*Primary Examiner* — Kenneth R Horlick
(74) *Attorney, Agent, or Firm* — Knobbe Martens Olson & Bear, LLP

(57) ABSTRACT

The present invention relates generally to an improved method of amplifying a nucleic acid region of interest and to primers for use therein. More particularly, the present invention is directed to an improved method of amplifying a nucleic acid region which has resulted from the recombination of two or more immunoglobulin or T cell receptor gene segments and primers for use therein. The method of the present invention is based on the determination that performing the amplification step at an annealing temperature determined relative to the critical annealing temperature unique to a given reaction and/or using optimised primers enables higher levels of sensitivity than have previously been achievable in the context of prior art methods of amplifying rearranged immunological or T cell receptor genes. The method of the present invention is particularly useful where the subject recombination target comprises only one N region. The provision of a highly sensitive yet simple means of detecting specific immunological and T cell receptor nucleic acid recombination events is useful in a range of applications including, but not limited to, the diagnosis and/or monitoring of clonal lymphoid cell populations or disease conditions which are characterised by specific V/D/J recombination events (such as detecting minimal residual disease in leukaemias) or the analysis or identification of immunological or T cell receptor gene regions of interest.

32 Claims, 6 Drawing Sheets

Specification includes a Sequence Listing.

SEQUENCE LISTING

<160> NUMBER OF SEQ ID NOS: 21

<210> SEQ ID NO 1
<211> LENGTH: 30
<212> TYPE: DNA
<213> ORGANISM: Artificial Sequence
<220> FEATURE:
<223> OTHER INFORMATION: AAMJ1b

<400> SEQUENCE: 1
ctttgctgag cacctgtccc caagtctgaa                    30

```
<210> SEQ ID NO 2
<211> LENGTH: 23
<212> TYPE: DNA
<213> ORGANISM: Artificial Sequence
<220> FEATURE:
<223> OTHER INFORMATION: AAMJ2

<400> SEQUENCE: 2
aggccggctg cagaccccag ata                                              23

<210> SEQ ID NO 3
<211> LENGTH: 26
<212> TYPE: DNA
<213> ORGANISM: Artificial Sequence
<220> FEATURE:
<223> OTHER INFORMATION: AAMJ3c

<400> SEQUENCE: 3
cccccggaca ttatctccca gctcca                                           26

<210> SEQ ID NO 4
<211> LENGTH: 34
<212> TYPE: DNA
<213> ORGANISM: Artificial Sequence
<220> FEATURE:
<223> OTHER INFORMATION: AAMJ4c

<400> SEQUENCE: 4
gcttatttcc ccccaaaaat gcagcaaaac cctt                                  34

<210> SEQ ID NO 5
<211> LENGTH: 32
<212> TYPE: DNA
<213> ORGANISM: Artificial Sequence
<220> FEATURE:
<223> OTHER INFORMATION: AAMJ5c

<400> SEQUENCE: 5
cctccaaaat gcctccaaga ctctgaccct ga                                    32

<210> SEQ ID NO 6
<211> LENGTH: 31
<212> TYPE: DNA
<213> ORGANISM: Artificial Sequence
<220> FEATURE:
<223> OTHER INFORMATION: AAMJ6c

<400> SEQUENCE: 6
aggaaacccc acaggcagta gcagaaaaca a                                     31

<210> SEQ ID NO 7
<211> LENGTH: 31
<212> TYPE: DNA
<213> ORGANISM: Artificial Sequence
<220> FEATURE:
<223> OTHER INFORMATION: TCR1.1b

<400> SEQUENCE: 7
ttccctgtga cggatctgca aagaacctg a                                      31

<210> SEQ ID NO 8
<211> LENGTH: 31
<212> TYPE: DNA
<213> ORGANISM: Artificial Sequence
<220> FEATURE:
```

<223> OTHER INFORMATION: TCR1.2b

<400> SEQUENCE: 8
ccctcctaga gacccccagc cttacctaca a                           31

<210> SEQ ID NO 9
<211> LENGTH: 31
<212> TYPE: DNA
<213> ORGANISM: Artificial Sequence
<220> FEATURE:
<223> OTHER INFORMATION: TCR1.3b

<400> SEQUENCE: 9
caagttccca gctgtccagc cttgacttac t                           31

<210> SEQ ID NO 10
<211> LENGTH: 39
<212> TYPE: DNA
<213> ORGANISM: Artificial Sequence
<220> FEATURE:
<223> OTHER INFORMATION: TCR1.4b

<400> SEQUENCE: 10
ccaggaactc cgaccttatg atacactatc ccgaaagaa                   39

<210> SEQ ID NO 11
<211> LENGTH: 34
<212> TYPE: DNA
<213> ORGANISM: Artificial Sequence
<220> FEATURE:
<223> OTHER INFORMATION: TCR1.5b

<400> SEQUENCE: 11
atggccatac caccctgatt ctgcaactta ccta                        34

<210> SEQ ID NO 12
<211> LENGTH: 28
<212> TYPE: DNA
<213> ORGANISM: Artificial Sequence
<220> FEATURE:
<223> OTHER INFORMATION: TCR1.6b

<400> SEQUENCE: 12
gagtcaagag tggagccccc atacctgt                               28

<210> SEQ ID NO 13
<211> LENGTH: 27
<212> TYPE: DNA
<213> ORGANISM: Artificial Sequence
<220> FEATURE:
<223> OTHER INFORMATION: TCR2.1b

<400> SEQUENCE: 13
cacctggagc ccccttctta cctagca                                27

<210> SEQ ID NO 14
<211> LENGTH: 21
<212> TYPE: DNA
<213> ORGANISM: Artificial Sequence
<220> FEATURE:
<223> OTHER INFORMATION: TCR2.2b

<400> SEQUENCE: 14
cggagcccca accgcctcct t                                      21

```
<210> SEQ ID NO 15
<211> LENGTH: 22
<212> TYPE: DNA
<213> ORGANISM: Artificial Sequence
<220> FEATURE:
<223> OTHER INFORMATION: TCR2.3b

<400> SEQUENCE: 15
ggagccccgc ttaccgagca ct                                               22

<210> SEQ ID NO 16
<211> LENGTH: 16
<212> TYPE: DNA
<213> ORGANISM: Artificial Sequence
<220> FEATURE:
<223> OTHER INFORMATION: TCR2.4b

<400> SEQUENCE: 16
ccggcggccc cagctt                                                      16

<210> SEQ ID NO 17
<211> LENGTH: 20
<212> TYPE: DNA
<213> ORGANISM: Artificial Sequence
<220> FEATURE:
<223> OTHER INFORMATION: TCR2.5b

<400> SEQUENCE: 17
gcgctcaccg agcaccagga                                                  20

<210> SEQ ID NO 18
<211> LENGTH: 22
<212> TYPE: DNA
<213> ORGANISM: Artificial Sequence
<220> FEATURE:
<223> OTHER INFORMATION: TCR2.5c

<400> SEQUENCE: 18
ccgcgctcac cgagcaccag ga                                               22

<210> SEQ ID NO 19
<211> LENGTH: 23
<212> TYPE: DNA
<213> ORGANISM: Artificial Sequence
<220> FEATURE:
<223> OTHER INFORMATION: TCR2.5d

<400> SEQUENCE: 19
cccgcgctca ccgagcacca gga                                              23

<210> SEQ ID NO 20
<211> LENGTH: 25
<212> TYPE: DNA
<213> ORGANISM: Artificial Sequence
<220> FEATURE:
<223> OTHER INFORMATION: TCR2.6b

<400> SEQUENCE: 20
cgcgaaaact cacccagcac ggtca                                            25

<210> SEQ ID NO 21
<211> LENGTH: 23
<212> TYPE: DNA
<213> ORGANISM: Artificial Sequence
<220> FEATURE:
<223> OTHER INFORMATION: TCR2.7d
```

```
<400> SEQUENCE: 21
ggaaggtggg gagacgcccg aat                                                    23
```

NUCLEIC ACID AMPLIFICATION METHOD AND PRIMERS FOR USE THEREIN

CROSS REFERENCE TO RELATED APPLICATIONS

This application is a U.S. National Phase Application of PCT International Application Number PCT/AU2019/050591, filed on Jun. 7, 2019, designating the United States of America and published in the English language, which is an International Application of and claims the benefit of priority to U.S. Provisional Patent Application No. 62/757,634, filed on Nov. 8, 2018 and U.S. Provisional Application No. 62/683,415, filed on Jun. 11, 2018. The disclosures of the above-referenced applications are hereby expressly incorporated by reference in their entireties.

REFERENCE TO SEQUENCE LISTING

A Sequence Listing submitted as an ASCII text file via EFS-Web is hereby incorporated by reference in accordance with 35 U.S.C. § 1.52(e). The name of the ASCII text file for the Sequence Listing is SeqList-WMRK6-006APC.txt, the date of creation of the ASCII text file is Jul. 17, 2019, and the size of the ASCII text file is 4 KB.

FIELD OF THE INVENTION

The present invention relates generally to an improved method of amplifying a nucleic acid region of interest and to primers for use therein. More particularly, the present invention is directed to an improved method of amplifying a nucleic acid region which has resulted from the recombination of two or more immunoglobulin or T cell receptor gene segments and primers for use therein. The method of the present invention is based on the determination that performing the amplification step at an annealing temperature determined relative to the critical annealing temperature unique to a given reaction and/or using optimised primers enables higher levels of sensitivity than have previously been achievable in the context of prior art methods of amplifying rearranged immunological or T cell receptor genes. The method of the present invention is particularly useful where the subject recombination target comprises only one N region. The provision of a highly sensitive yet simple means of detecting specific immunological and T cell receptor nucleic acid recombination events is useful in a range of applications including, but not limited to, the diagnosis and/or monitoring of clonal lymphoid cell populations or disease conditions which are characterised by specific V/D/J recombination events (such as detecting minimal residual disease in leukaemias) or the analysis or identification of immunological or T cell receptor gene regions of interest.

BACKGROUND OF THE INVENTION

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification.

Bibliographic details of the publications referred to by author in this specification are collected alphabetically at the end of the description.

A clone is generally understood as a population of cells which has descended from a common precursor cell. Diagnosis and/or detection of the existence of a clonal population of cells or organisms in a subject has generally constituted a relatively problematic procedure. Specifically, a clonal population may constitute only a minor component within a larger population of cells or organisms. For example, in terms of the mammalian organism, one of the more common situations in which detection of a clonal population of cells is required occurs in terms of the diagnosis and/or detection of neoplasms, such as cancer. However, detection of one or more clonal populations may also be important in the diagnosis of conditions such as myelodysplasia or polycythaemia vera and also in the detection of antigen driven clones generated by the immune system.

Generally, the population within which the clone arises corresponds to a population of cells within a particular tissue or compartment of the body. Nevertheless, despite the fact that sampling such a population of cells effectively narrows the examination to a sub group of cells or organisms, this may nevertheless still present a clinician with a large background population of non-clonal cells or organisms within which the clonal population must be identified.

If the members of the clone are characterized by a molecular marker, such as an altered sequence of DNA, then the problem of detection may be able to be translated into the problem of detecting a population of molecules which all have the same molecular sequence within a larger population of molecules which have a different sequence, either all being the same and different, or being heterogeneous to a greater or lesser extent. The level of detection of the marker molecules that can be achieved is very dependent upon the sensitivity and specificity of the detection method, but nearly always, when the proportion of target molecules within the larger population of molecules becomes small, the signal noise from the larger population makes it impossible to detect the signal from the target molecules.

A specific class of molecular markers which, although highly specific, present unique complexities in terms of its detection are those which result from genetic recombination events.

Recombination of the genetic material in somatic cells involves the bringing together of two or more regions of the genome which are initially separate. It may occur as a random process but it also occurs as part of the developmental process in normal lymphoid cells.

In relation to cancer, recombination may be simple or complex. A simple recombination may be regarded as one in which two unrelated genes or regions are brought into apposition. A complex recombination may be regarded as one in which more than two genes or gene segments are recombined. The classical example of a complex recombination is the rearrangement of the immunoglobulin (Ig) and T-cell receptor (TCR) variable genes which occurs during normal development of lymphoid cells and which involves recombination of the V, D and J gene segments. The loci for these gene segments are widely separated in the germline but recombination during lymphoid development results in apposition of V, D and J gene segments, or V and J gene segments, with the junctions between these gene segments being characterised by small regions of insertion and deletion of nucleotides ($N_1$ and $N_2$ regions). This process occurs randomly so that each normal lymphocyte comes to bear a unique V(D)J rearrangement which may be a complete VDJ rearrangement or a VJ or DJ rearrangement, depending both on the gene which is rearranged and on the nature of the rearrangement. Since a lymphoid cancer, such as acute lymphoblastic leukaemia, chronic lymphocytic leukaemia, lymphoma or myeloma, occurs as the result of neoplastic change in a single normal cell, all of the cancer cells will, at least originally, bear the junctional V(D)J rearrangement originally present in the founder cell. Subclones may arise during expansion of the neoplastic population and further V(D)J rearrangements may occur in them.

The unique DNA sequences resulting from recombination and which are present in a cancer clone or subclone provide a unique genetic marker which can be used to monitor the response to treatment and to make decisions on therapy. Monitoring of the clone can be performed by PCR, flow cytometry or next-gen sequencing. Monitoring by flow cytometry involves the determination of the immunophenotype of the cancer cells at diagnosis and searching for the same phenotype in subsequent samples in order to detect and quantify the cancer cells. Next-gen sequencing is a newer approach, the strengths and weaknesses of which are still being evaluated. However, this is also a costly technique.

PCR-based analysis is a preferred method due to its potentially high level of specificity and automation. Quantification by PCR conventionally involves sequencing of the marker rearrangement using DNA from a sample taken at the time of diagnosis, synthesis of patient-specific primers and use of these primers in a PCR on DNA extracted from samples obtained during treatment. Usually, two primers are placed on either side of the site of recombination, typically with the downstream primer being directed to the J gene segment and the upstream primer (which is also known as the allele specific oligonucleotide [ASO], being designed to be directed to the most variable region of the rearrangement (Bruggemann et al, 2004; Pongers-Willemse et al, 1999; Nakao et al, 2000; van der Velden et al, 2002; van der Velden et al, 2004; van der Velden et al, 2007; van der Velden et al, 2009; van der Velden et al, 2014; Verhagen et al, 2000). Occasionally the upstream primer is directed to the V gene segment and the ASO primer is downstream and is directed to the most variable region of the rearrangement. The non-ASO primer is thus a consensus primer as it is directed to a conserved region which is common to many different rearrangements.

Monitoring by PCR of minimal residual disease (MRD) in leukaemia has become widely used in clinical practice. Typically, decisions are made on whether to continue or change treatment by measuring the number of leukaemic cells (MRD) at the end of induction treatment (approximately one month) and after several cycles of consolidation treatment (approximately 80 days). Typically, a decision may be made to increase the intensity of treatment if the level of MRD at the end of induction is above a defined cut-off level. This cut-off level varies slightly between different group protocols but is typically between $10^{-3}$ (1/1000) and $10^{-4}$ (1/10,000) leukaemic cells/total cells.

The problem which currently exists with this method is nonspecificity which may give rise to false positive results and which, importantly, limits sensitivity of detection and measurement. As a result, it is sometimes not possible to detect, and often not possible to quantify, MRD below a level of $10^{-4}$. This has two consequences:

When MRD is below the limit of detection, quantification is impossible. This is the case for many patients. There is great interest in attempting to identify patients who have responded very well to initial treatment and in whom the intensity of subsequent treatment can be decreased. Such patients would be characterised by having very low levels of MRD e.g. <$10^{-6}$, but, if the limit of detection is $10^{-4}$, they cannot be distinguished from patients with levels between $10^{-4}$ and $10^{-6}$.

Owing to stochastic variation in the assay, the precision of measurement is poor when the level of MRD is close to but still above the limit of detection.

Factors leading to nonspecificity include:

The sequences to which the two primers bind are not unique but are sequences normally present in the genome and the specificity of amplification only arises because of the rearrangement bringing the binding sequences close to each other.

Some degree of homology is present between different members of the V gene family and also between different members of the D gene family. This increases the probability of the upstream primer hybridising to a nonleukaemic rearrangement.

The rearrangements in the population of nonleukaemic lymphocytes are extremely heterogeneous so that there is a real probability that a rearrangement in one or more cells in the normal population will resemble the universal rearrangement in the population of leukaemic cells.

There are many prior art methods which, over the last 18 years, have attempted to minimise the incidence of nonspecific amplification. These include:

The performance of a 2-round or 3-round nested PCR using a series of upstream primers targeted to different regions of the rearranged target gene. The targeted regions typically comprise two N regions. This eliminates nonspecificity and results in a highly sensitive assay (e.g. Morley et al, 2009). However, this approach is more complex and carries the risk of environmental contamination with PCR product.

Replacement of PCR by next-gen sequencing. This procedure can possibly measure MRD down to $10^{-5}$ and, perhaps with extra steps, down to $10^{-6}$. However, the procedure is complex and expensive, particularly if high sensitivity is desired.

Using improved flow cytometry.

Designing the 3' end of the allele-specific (ASO) primer in an attempt to minimise nonspecificity. It is a widely held belief that it is desirable to include a G or C base at the 3' end of a PCR primer in order to have efficient amplification. Specifically, efficient primer hybridisation and extension is favoured by the presence of one or more G or C bases at the 3' end as these bases form a stronger hydrogen bond to their complementary base then do A or T bases Directing the upstream ASO primer to the largest N region and the downstream primer to the germline J sequence, coupled with annealing temperatures of approximately 60° C. (e.g. Bruggemann et al, 2004; Pongers-Willemse et al, 1999; Nakao et al, 2000; van der Velden et al, 2002; van der Velden et al, 2004; van der Velden et al, 2007; van der Velden and van Dongen, 2009; van der Velden et al, 2014; Verhagen et al, 2000).

The use of primers with Tm up to around 65° C. and/or the use of annealing temperatures of up to 69° C. (Bruggemann et al, 2004; Pongers-Willemse et al, 1999; Nakao et al, 2000; van der Velden et al, 2002; van der Velden et al, 2007; van der Velden and van Dongen, 2009; van der Velden et al, 2014; Verhagen et al, 2000).

The use of shortened primers.

Performing a touch-down PCR (Pongers-Willemse et al, 1999; Nakao et al 2000)

Designing the primers to exhibit specific placement characteristics in the context of their positioning on the rearranged gene.

Performing melting curve analysis in an effort to distinguish specific amplicons from non-specific amplicons. However, melting curve analysis fails when one of the primers is a consensus primer However, these methods, pursued over almost two decades, have failed to significantly reduce non-specific amplification (Bruggemann et al, 2004; Pongers-Willemse et al, 1999; Nakao et al, 2000; van der Velden et al, 2002; van der Velden et al, 2007; van der Velden et al, 2009; van der Velden et al, 2014; Verhagen et al, 2000). In fact, non-specific amplification has been accepted, as an unavoidable occurrence, to such an extent that the criteria for interpreting an MRD result recommend relating that result to the level of non-specificity that has been observed (van der Velden et al, 2007).

Accordingly, there is an ongoing need to develop improved amplification methods which are simple, yet exhibit improved sensitivity by virtue of a reduction in the level of non-specific amplification of the rearranged Ig and TCR genes, such as in the context of MRD.

In work leading up to the present invention, a highly sensitive one-round PCR has been developed based on the use of an annealing temperature which is determined reaction by reaction based on the performance of the primers which are selected for use in a given reaction. Specifically, performing the subject reaction at an annealing temperature within the range of 3° C. below the critical annealing temperature (Tc) and up to the Tc of that reaction, produces such a significant reduction in non-specific amplification as to enable quantification of MRD in samples obtained during treatment of patients with acute lymphoblastic leukaemia or chronic lymphocytic leukaemia, this having not been achievable to date. These findings contrast to virtually all prior art methods which are based on the selection of an annealing temperature determined at a fixed value for all reactions, rather than an annealing temperature which has been experimentally determined by reference to the functionality of the primer selected for use in a given reaction.

It has been still further determined that the design and use of primers wherein one of more of the nucleotides at the terminal 3' end of the primer are an A and/or T, when used either in its own right or in combination with an annealing temperature selected in accordance with the method of the present invention, also significantly reduces non-specific amplification. When designed to also include a melting curve analysis, the method of the present invention becomes a particularly sensitive, and therefore powerful, tool.

The developments of the present invention, although applicable to any Ig or TCR rearrangement analysis has been determined to demonstrate particular efficacy with respect to the amplification of Ig or T cell recombination target regions which comprise only one N region.

These findings are both unexpected and counterintuitive when considered in light of the limited improvements which have been achieved to date based on variations to primer design, annealing temperature and PCR conditions, all of which have hitherto been tested with limited success. The development of this highly sensitive method obviates the need to perform more complex multiplex or nested PCR reactions or to otherwise use highly expensive next-gen sequencing. The development of the present method has now enabled the improved detection and/or monitoring of clonal populations of lymphoid cells which are characterised by a specific Ig or TCR gene recombination, such as neoplastic populations of T cells or B cells. There is also provided means of diagnosing and/or monitoring disease conditions which may be characterised by the expansion of such clonal populations of cells.

SUMMARY OF THE INVENTION

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The present invention is not to be limited in scope by the specific embodiments described herein, which are intended for the purposes of exemplification only. Functionally-equivalent products, compositions and methods are clearly within the scope of the invention, as described herein.

As used herein, the term "derived from" shall be taken to indicate that a particular integer or group of integers has originated from the species specified, but has not necessarily been obtained directly from the specified source. Further, as used herein the singular forms of "a", "and" and "the" include plural referents unless the context clearly dictates otherwise.

The subject specification contains nucleotide sequence information prepared using the programme PatentIn Version 3.1, presented herein after the bibliography. Each nucleotide sequence is identified in the sequence listing by the numeric indicator <210> followed by the sequence identifier (e.g. <210>1, <210>2, etc). The length, type of sequence (DNA, etc) and source organism for each nucleotide sequence are indicated by information provided in the numeric indicator fields <211>, <212> and <213>, respectively. Nucleotide sequences referred to in the specification are identified by the indicator SEQ ID NO: followed by the sequence identifier (e.g. SEQ ID NO:1, SEQ ID NO:2, etc.). The sequence identifier referred to in the specification correlates to the information provided in numeric indicator field <400> in the sequence listing, which is followed by the sequence identifier (e.g. <400>1, <400>2, etc.). That is SEQ ID NO:1 as detailed in the specification correlates to the sequence indicated as <400>1 in the sequence listing.

One aspect of the present invention is directed to a method of amplifying an Ig or TCR nucleic acid region which is characterised by the rearrangement of two or more V, D or J gene segments said method comprising contacting a nucleic acid sample of interest with forward and reverse primers directed to said rearranged Ig or TCR nucleic acid region and amplifying said nucleic acid sample using:

(i) an annealing temperature within the range between Tc and (Tc-3° C.) of the subject amplification reaction; and/or (ii) at least one primer which comprises at least one A and/or T nucleotide at the 3' terminal nucleotide position;

and optionally a means to conduct a melting curve analysis.

In another aspect there is provided a method of amplifying an Ig or TCR DNA region which is characterised by the rearrangement of two or more V, D or J gene segments said method comprising contacting a nucleic acid sample of interest with forward and reverse primers directed to said rearranged Ig or TCR nucleic acid region and amplifying said nucleic acid sample using:

(i) an annealing temperature within the range between Tc and (Tc-3° C.) of the subject amplification reaction; and/or
(ii) at least one primer which comprises at least one A and/or T nucleotide at the 3' terminal nucleotide position of said primer;
and optionally a means to conduct a melting curve analysis.

In still another aspect there is provided a method of amplifying an Ig or TCR nucleic acid region which is characterised by the rearrangement of two or more V, D or J gene segments, which rearrangement is characterised by only one N region, said method comprising contacting a nucleic acid sample of interest with forward and reverse primers directed to said rearranged Ig or TCR nucleic acid region and amplifying said nucleic acid sample using:
(i) an annealing temperature within the range between Tc and (Tc-3° C.) of the subject amplification reaction; and/or
(ii) at least one primer which comprises at least one A and/or T nucleotide at the 3' terminal nucleotide position of said primer;
and optionally a means to conduct a melting curve analysis.

In accordance with these aspects, in one embodiment, said at least one primer is the ASO primer.

In another embodiment, said method comprises using both an annealing temperature within the range between Tc and (Tc-3° C.) of the subject amplification reaction and one or more primers which comprise an A or T nucleotide at the 3' terminal nucleotide position of said primer.

In still another embodiment, said nucleic acid is DNA.

In yet another embodiment there is an A and/or T nucleotide at each of the two most 3' terminal nucleotide positions of said primer. In another embodiment there is an A and/or T nucleotide at each of the three most 3' terminal nucleotide positions of said primer. In yet another embodiment there is an A and/or T nucleotide at each of the four most 3' terminal nucleotide positions of the primer. In still yet another embodiment there is an A and/or T nucleotide at each of the five most 3' terminal nucleotide positions of the primer. In yet still another embodiment there is an A and/or T nucleotide at each of the six most 3' terminal nucleotide positions of the primer.

In still yet another embodiment a melting curve analysis is performed.

In a further embodiment, said amplification is polymerase chain reaction.

Yet another aspect of the present invention provides a method of detecting and/or monitoring a clonal population of cells in a mammal, which clonal cells are characterised by an Ig or TCR nucleic acid region which is characterised by the rearrangement of two or more V, D or J gene segments, said method comprising:
(i) contacting the DNA material of a biological sample derived from a mammal with the forward and reverse primers as hereinbefore defined for a time and under conditions sufficient to facilitate interaction of said primers with said target nucleic acid molecule;
(ii) amplifying said nucleic acid target using (a) an annealing temperature within the range between Tc and (Tc-3° C.) of the subject amplification reaction; and/or (b) at least one primer which comprises at least one A and/or T nucleotide at the 3' terminal nucleotide position of said primer; and optionally a means to conduct a melting curve analysis; and
(iii) detecting said amplified product.

In accordance with this aspect, in one embodiment, said at least one primer is the ASO primer.

In another embodiment, said method comprises using both an annealing temperature within the range between Tc and (Tc-3° C.) of the subject amplification reaction and at least one primer which comprise an A or T nucleotide at the 3' terminal nucleotide position of said primer.

In still another embodiment, said nucleic acid is DNA.

In yet another embodiment there is an A and/or T nucleotide at each of the two most 3' terminal nucleotide positions of said primer. In another embodiment there is an A and/or T nucleotide at each of the three most 3' terminal nucleotide positions of said primer. In yet another embodiment there is an A and/or T nucleotide at each of the four most 3' terminal nucleotide positions of the primer. In still yet another embodiment there is an A and/or T nucleotide at each of the five most 3' terminal nucleotide positions of the primer. In yet still another embodiment there is an A and/or T nucleotide at each of the six most 3' terminal nucleotide positions of the primer.

In still yet another embodiment a melting curve analysis is performed.

In a further embodiment, said amplification reaction is polymerase chain reaction.

In yet still another embodiment, said primer directed to the downstream gene segment is directed to the J segment.

In a further aspect said condition is a neoplasia and even more preferably a lymphoid neoplasia.

In another aspect, the method of the present invention is used to detect minimum residual disease in the context of lymphoid leukaemias.

Yet another aspect of the present invention is directed to an isolated primer as hereinbefore described.

Yet still another aspect of the present invention is directed to a kit for facilitating the identification of an Ig or TCR nucleic acid region which is characterised by the rearrangement of two or more V, D or J gene segments, said kit comprising compartments adapted to contain any one or more of the oligonucleotide primers as hereinbefore defined, reagents useful for facilitating interaction of said primer with the target nucleic acid molecule and reagents useful for enabling said interaction to result in amplification of said nucleic acid target

DETAILED DESCRIPTION OF THE INVENTION

Figure 1:
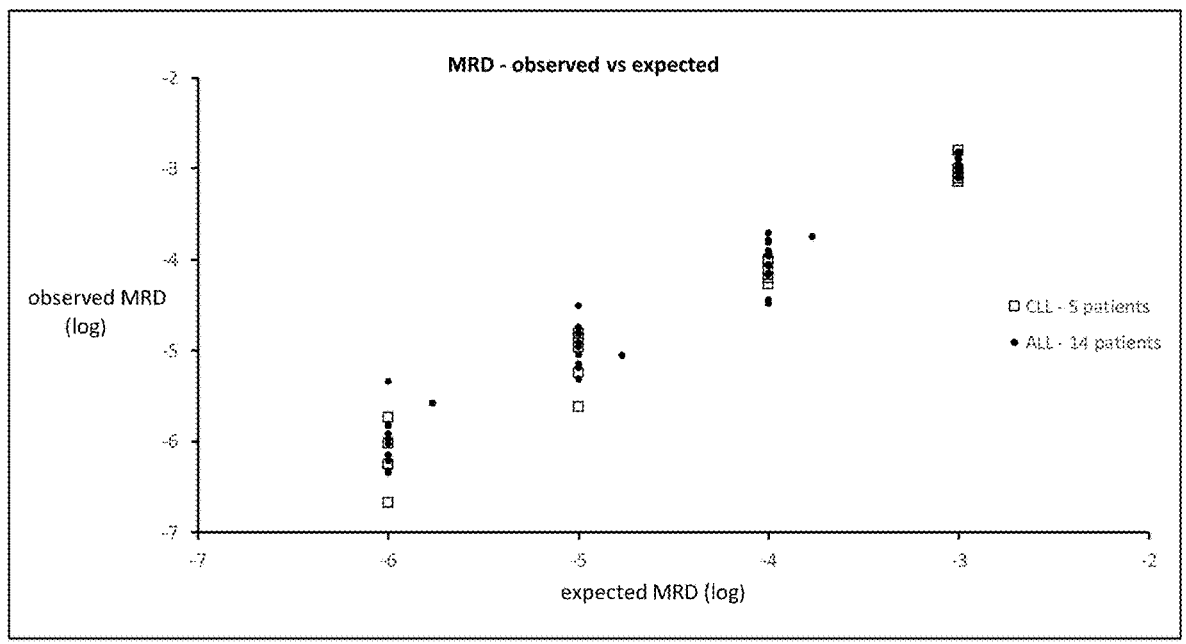
FIG. 1 is a graphical representation of the observed MRD values versus expected MRD values. Leukemic DNA and non-leukemic DNA were mixed in various known proportions to provide artificial samples containing a range of levels of MRD. Thirty μg of DNA from each sample were assayed and the levels of MRD observed are related in the Figure to the expected value. Note that with assay of this amount of DNA the limit of detection of MRD is below $10^{-6}$. ALL refers to DNA from patients with acute lymphoblastic leukaemia, CLL refers to DNA from patients with chronic lymphocytic leukaemia.
Figure 2:
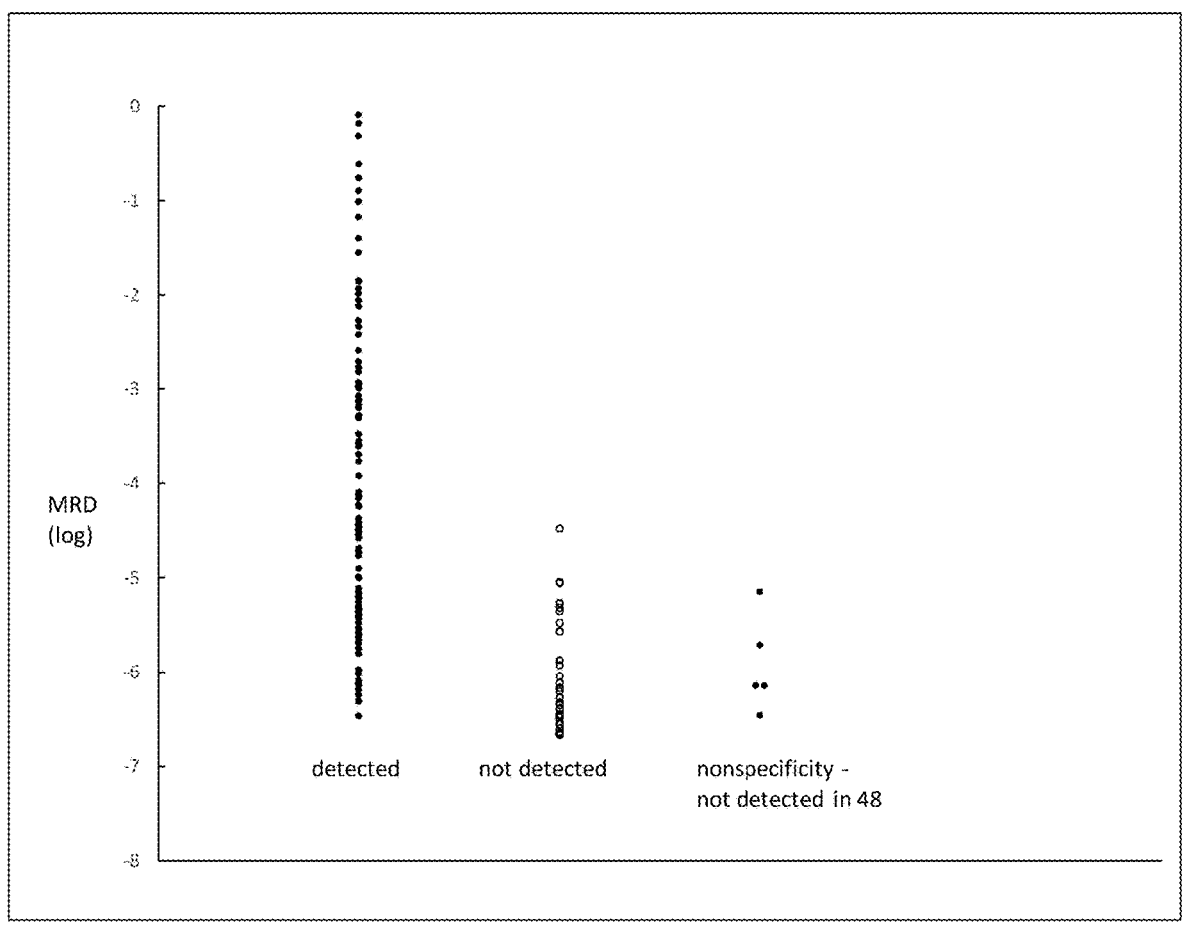
FIG. 2 is a graphical representation of the results obtained of measurement of MRD in samples of blood from patients with acute lymphoblastic leukaemia. The left-hand column shows levels that were detected and measured. The middle column shows the results for samples in which MRD was not detected; the level of MRD was less than the value indicated and the variation in the value shown resulted from variation in the amount of DNA available for study. The right-hand column shows the level of nonspecificity that was observed with primers from a total of 53 patients. Nonspecificity was observed with 5 primer pairs and the levels are shown. Nonspecificity was not observed with primers from 48 patients indicating that the level was less than $3.4 \times 10^{-7}$.

The present invention is predicated, in part, on the development of a simple yet highly sensitive amplification method for detecting a clonal population of cells characterised by a rearranged Ig or TCR gene. The use of an annealing temperature within the range of the Tc through to 3° C. below the Tc ("Tc-3° C.") of the PCR reaction in issue has unexpectedly enabled the development of a highly sensitive single round PCR, particularly if coupled with a melting curve analysis as part of the amplification process. Still further, the use of primers designed such that at least the terminal 3' nucleotide position of the primer is an A and/or T, when used either in its own right or in combination with an annealing temperature selected in accordance with the method of the present invention still further improves the sensitivity and specificity of the amplification reaction. The development of this method has now facilitated the detection of specific Ig or TCR gene rearrangements of interest, in particular in the context of detecting rearrangements which are characterised by only one N region. This has enabled the improved monitoring of conditions characterised by the presence of cells, such as clonal populations of cells, expressing a known Ig or TCR gene rearrangement. The methods and primers of the present invention find particular use with respect to the detection of minimal residual disease, which requires high levels of sensitivity and specificity, this currently generally only being achievable via the application of highly complex and expensive molecular techniques.

Accordingly, one aspect of the present invention is directed to a method of amplifying an Ig or TCR nucleic acid region which is characterised by the rearrangement of two or more V, D or J gene segments said method comprising contacting a nucleic acid sample of interest with forward and reverse primers directed to said rearranged Ig or TCR nucleic acid region and amplifying said nucleic acid sample using:

(i) an annealing temperature within the range between Tc and (Tc-3° C.) of the subject amplification reaction; and/or (ii) at least one primer which comprises at least one A and/or T nucleotide at the 3' terminal nucleotide position of said primer;

and optionally a means to conduct a melting curve analysis.

In one embodiment, said at least one primer is the ASO primer.

In another embodiment, said method comprises using both an annealing temperature within the range between Tc and (Tc-3° C.) of the subject amplification reaction and one or more primers which comprise an A or T nucleotide at the 3' terminal nucleotide position of said primer.

In yet another embodiment, a melting curve analysis is performed.

Reference to an "Ig or TCR nucleic acid region" should be understood as a reference to any region of Ig or TCR DNA or RNA which is sought to be amplified. Said nucleic acid region may correspond to a partially rearranged gene or a fully rearranged gene.

Reference to a "nucleic acid" or "nucleotide" or "base" should be understood as a reference to both deoxyribonucleic acid or nucleotides and ribonucleic acid or nucleotides or purine or pyrimidine bases or derivatives or analogues thereof. In this regard, it should be understood to encompass phosphate esters of ribonucleotides and/or deoxyribonucleotides, including DNA (cDNA or genomic DNA), RNA or mRNA among others. The nucleic acid molecules of the present invention may be of any origin including naturally occurring (such as would be derived from a biological sample), recombinantly produced or synthetically produced. The base may also be a non-standard base such as inosine.

Reference to "derivatives" should be understood to include reference to fragments, parts, portions, homologs and mimetics of said nucleic acid molecules from natural, synthetic or recombinant sources. "Functional derivatives" should be understood as derivatives which exhibit any one or more of the functional activities of purine or pyrimidine bases, nucleotides or nucleic acid molecules. The derivatives of said nucleotides or nucleic acid sequences include fragments having particular regions of the nucleotide or nucleic acid molecule fused to other proteinaceous or non-proteinaceous molecules. "Analogs" contemplated herein include, but are not limited to, modifications to the nucleotide or nucleic acid molecule such as modifications to its chemical makeup or overall conformation. This includes, for example, modification to the manner in which nucleotides or nucleic acid molecules interact with other nucleotides or nucleic acid molecules such as at the level of backbone formation or complementary base pair hybridisation. A locked nucleic acid is an example of an analog as herein defined. The biotinylation of a nucleotide or nucleic acid molecules is an example of a "functional derivative" as herein defined. Derivatives of nucleic acid molecules may be derived from single or multiple nucleotide substitutions, deletions and/or additions. The term "functional derivatives" should also be understood to encompass nucleotides or nucleic acid exhibiting any one or more of the functional activities of a nucleotide or nucleic acid sequence, such as for example, products obtained following natural product screening.

The subject "nucleic acid" region may be DNA or RNA or derivative or analogue thereof. Since the region of interest is a DNA sequence which encodes a proteinaceous molecule it may take the form of genomic DNA, cDNA which has been generated from a mRNA transcript, or DNA generated by nucleic acid amplification. If the subject method is directed to detecting a region of RNA, it would be appreciated that it will first be necessary to reverse transcribe the RNA to DNA, such as using RT-PCR. The subject RNA may be any form of RNA, such as mRNA, primary RNA transcript, ribosomal RNA, transfer RNA, micro RNA or the like. Preferably, said nucleic acid region of interest is a DNA region of interest. To this end, said DNA includes DNA generated by reverse transcription from RNA which is ultimately the subject of analysis, and DNA generated by a nucleic acid amplification method such as PCR.

The nucleic acid region which is the subject of amplification is an Ig or TCR nucleic acid region which has undergone the rearrangement of two or more of the V, D or J gene segments. Accordingly, the subject nucleic acid region of interest may correspond to either a partially or fully rearranged gene. As discussed in more detail hereafter, Ig and TCR rearrangement occurs as a series of sequential rearrangements which result in a fully rearranged variable region which is, in the last step, rearranged to join a constant region gene. The method of the present invention may be amplifying all or part of a partially rearranged gene, depending on the point at which the clonal lymphoid cell may have ceased differentiation.

In one embodiment, said target nucleic acid region is DNA.

According to this embodiment, there is provided a method of amplifying an Ig or TCR DNA region which is characterised by the rearrangement of two or more V, D or J gene segments said method comprising contacting a nucleic acid sample of interest with forward and reverse primers directed to said rearranged Ig or TCR nucleic acid region and amplifying said nucleic acid sample using:

(i) an annealing temperature within the range between Tc and (Tc-3° C.) of the subject amplification reaction; and/or (ii) at least one primer which comprises at least one A and/or T nucleotide at the 3' terminal nucleotide position of said primer;

and optionally a means to conduct a melting curve analysis.

In another embodiment, said at least one primer is the ASO primer.

In still another embodiment, said method comprises using both an annealing temperature within the range between Tc and (Tc-3° C.) of the subject amplification reaction and at least one primer which comprises an A or T nucleotide at the 3' terminal nucleotide position of said primer n.

In yet another embodiment, a melting curve analysis is performed.

The method of the present invention is effected by contacting the nucleic acid sample to be tested with forward and reverse primers. Reference to a "primer" or an "oligonucleotide primer" should be understood as a reference to any molecule comprising a sequence of nucleotides, or functional derivatives or analogues thereof, the function of which includes hybridisation to a region of a nucleic acid molecule of interest. The primer may contain one or more locked nucleic acids. It should also be understood that the primer may comprise non-nucleic acid components. For example, the primer may also comprise a non-nucleic acid tag such as a fluorescent or enzymatic tag or some other non-nucleic acid component which facilitates the use of the molecule as a probe or which otherwise facilitates its detection or immobilisation. The primer may also comprise additional nucleic acid components, such as an oligonucleotide tag. In another example, the primer may be a protein nucleic acid which comprises a peptide backbone exhibiting nucleic acid side chains. Preferably, said oligonucleotide primer is a DNA primer. The primers of the present invention are "directed to" a rearranged Ig or TCR nucleic acid. By "directed to" is meant that the primers are designed to hybridise, either partially or in their entirety, to the rearranged Ig or TCR nucleic acid region which is sought to be amplified.

Without limiting the present invention to any one theory or mode of action, V(D)J recombination in organisms with an adaptive immune system is an example of a type of site-specific genetic recombination that helps immune cells rapidly diversify to recognise and adapt to new pathogens. Each lymphoid cell undergoes somatic recombination of its germ line variable region gene segments (either V and J, D and J or V, D and J segments) depending on the particular gene segments rearranged in order to generate a total antigen diversity of approximately $10^{16}$ distinct variable region structures. In any given lymphoid cell, such as a T cell or B cell, at least two distinct variable region gene segment rearrangements are likely to occur due to the rearrangement of two or more of the two chains comprising the TCR or immunoglobulin molecule, specifically, the α, β, γ or δ chains of the TCR and/or the heavy and light chains of the immunoglobulin molecule. In addition to rearrangements of the VJ, DJ or VDJ segment of any given immunoglobulin or TCR gene, nucleotides are randomly removed and/or inserted at the junction between the segments. This leads to the generation of enormous diversity.

The loci for these gene segments are widely separated in the germline but recombination during lymphoid development results in apposition of a V, (D) and J gene, with the junctions between these genes being characterised by small regions of insertion and deletion of nucleotides. This process occurs randomly so that each normal lymphocyte comes to bear a unique V(D)J rearrangement. Since a lymphoid cancer, such as acute lymphoblastic leukaemia, chronic lymphocytic leukaemia, lymphoma or myeloma, occurs as the result of neoplastic change in a single normal cell, all of the cancer cells will, at least originally, bear the junctional V(D)J rearrangement originally present in the founder cell. Subclones may arise during expansion of the neoplastic population and further V(D)J rearrangements may occur in them.

Reference to a "gene segment" should be understood as a reference to the V, D and J regions of the immunoglobulin and T cell receptor genes. The V, D and J gene segments are clustered into families. For example, there are 52 different functional V gene segments for the κ immunoglobulin light chain and 5 J gene segments. For the immunoglobulin heavy chain, there are 55 functional V gene segments, 23 functional D gene segments and 6 J gene segments. Across the totality of the immunoglobulin and T cell receptor V, D and J gene segment families, there are a large number of individual gene segments, thereby enabling enormous diversity in terms of the unique combination of V(D)J rearrangements which can be effected. For the sake of clarity, the rearranged immunoglobulin or T cell receptor [V(D)J] variable nucleic acid region will be referred to herein as a "gene" and the individual V, D or J nucleic acid regions will be referred to as "gene segments". Accordingly, the terminology "gene segment" is not exclusively a reference to a segment of a gene. Rather, in the context of Ig and TCR gene rearrangement, it is a reference to a gene in its own right with these gene segments being clustered into families. A "rearranged"

immunoglobulin or T cell receptor variable region gene should be understood herein as a gene in which two or more of one V segment, one J segment and one D segment (if a D segment is incorporated into the particular rearranged variable gene in issue) have been spliced together to form a single rearranged "gene". In fact, this rearranged "gene" is actually a stretch of genomic DNA comprising one V gene segment, one J gene segment and one D gene segment which have been spliced together. It is therefore sometimes also referred to as a "gene region" (although not in the context of this specification) since it is actually made up of 2 or 3 distinct V, D or J genes (herein referred to as gene segments) which have been spliced together. The individual "gene segments" of the rearranged immunoglobulin or T cell receptor gene are therefore defined as the individual V, D and J genes. These genes are discussed in detail on the IMGT database. The term "gene" will be used herein to refer to the rearranged immunoglobulin or T cell receptor variable gene. The term "gene segment" will be used herein to refer to the V, D, J and framework 3 regions. However, it should be noted that there is significant inconsistency in the use of "gene"/"gene segment" language in terms of immunoglobulin and T cell receptor rearrangement. For example, the IMGT refers to individual V, D and J "genes", while some scientific publication refers to these as "gene segments". Some sources refer to the rearranged variable immunoglobulin or T cell receptor as a "gene region" while others refer to it as a "gene". The nomenclature which is used in this specification is as defined earlier.

Still without limiting the present invention to any one theory or mode of action, the nature of genetic recombination events is such that a junction between the recombined genes or gene segments (as defined herein) may be characterised by the deletion and insertion of random nucleotides resulting in the formation of "N regions". These N regions are also unique and are therefore useful targets in the context of the design of the primers of the present invention. In this regard, in order to simplify the discussion in this document in relation to subregions of the primers of the present invention relative to the genes/gene segments to which they bind, these N regions may alternatively be referred to as "gene segments" in the context of the present invention, despite the fact that they do not exist in the chromosome as a discrete gene segment and are generated only at the time of rearrangement due to the insertion and deletion of nucleotides at the site of recombination. The election to refer to these as either N gene segments or N regions is made purely on the basis of simplifying the language of any given section of this document in order to assist with clarity. Accordingly, in the context of V(D)J rearrangement in particular, the gene segments which may be the subject of analysis are the individual V, $N_1$, D, $N_2$ and J regions, as well as the framework 3 gene segment. In this context, the N gene segment between the V and D gene segments is termed $N_1$ and the N gene segment between the D and J gene segments is termed $N_2$. However, it should also be understood that N regions (or "gene segments") may occur within a V, D or J gene segment. Without limiting the present invention to any one theory of mode of action, this is most commonly observed in the context of the D gene segment which, during its rearrangement with the J gene segment can undergo the formation of one or more N regions within the D gene segment. Accordingly, although a fully rearranged VDJ region will generally always include N1 and N2 gene segments, it may also include additional N regions, such as within the V, D or J gene segments or, even, at the junction of the rearranged J gene segment and the constant gene, this final rearrangement usually occurring after the conclusion of the VDJ rearrangement.

Reference to "forward primer" (or "upstream primer") should be understood as a reference to a primer which amplifies the target nucleic acid (e.g. DNA) in the nucleic acid (e.g. DNA) sample of interest by hybridising to the antisense strand of the target DNA and 5' to the other primer.

Reference to "reverse primer" (or "downstream primer") should be understood as a reference to a primer which amplifies the target nucleic acid (e.g. DNA) in the nucleic acid (e.g. DNA) sample of interest and in the PCR by hybridising to the sense strand of the target nucleic acid (e.g. DNA) or 3' to the other primer.

While generally the forward or upstream primer is the ASO primer and the downstream or reverse primer is a consensus primer directed towards, for example, the conserved J region, in occasional situations the converse occurs, such that the forward primer is directed towards a conserved sequence of the V region, for example, and the reverse primer is the ASO primer.

The means to design and synthesise primers suitable for use in the present invention would be well known to those of skill in the art. As detailed hereinbefore, the V, D and J gene segment families have been fully identified and sequenced. Accordingly, the design of primers to amplify specific segments or combinations of rearranged segments is well within the skill of the person in the art. Nevertheless, substantial exemplification is also provided in Examples 1 and 2 in relation to the design and testing of primers which exhibit the Tc values hereby referenced.

Figure 3:
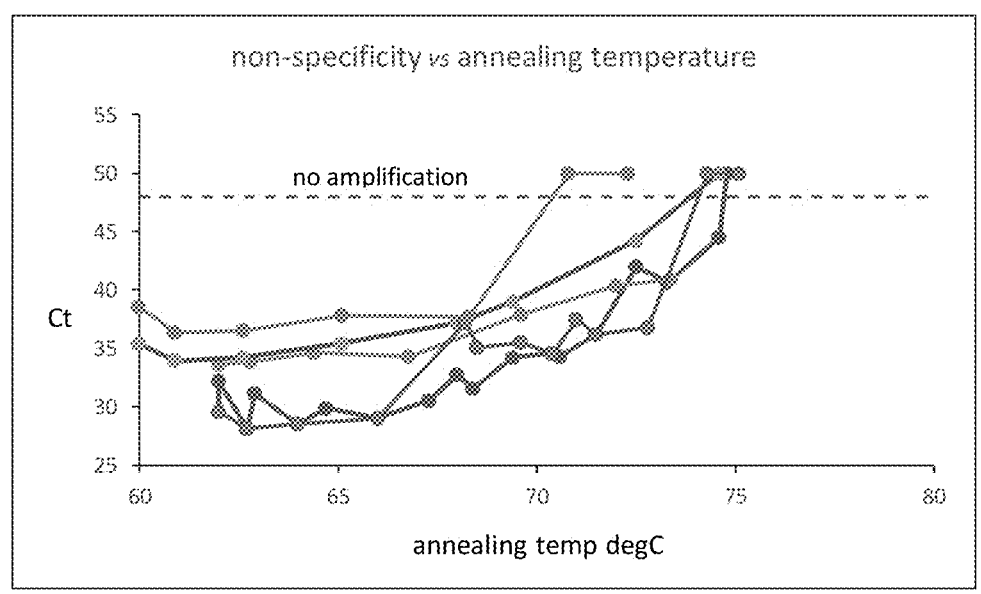
FIG. 3 is a graphical representation of non-specificity vs annealing temperature. PCR was performed using 2 µg non-leukaemic DNA and primer pairs from 5 patients. These primers were chosen for study as they showed some non-specificity at lower temperatures. The amount of non-specificity is inversely proportional to the Ct value. In each case the amount of non-specificity remained approximately the same until the annealing temperature increased above 70° C. It then progressively decreased and eventually could not be detected with 4 of the primer pairs.

As detailed hereinbefore, the method of the present invention is based on the determination that when the annealing temperature of an amplification reaction is selected by reference to the critical annealing temperature, which is unique to each reaction defined by a unique set of primers, a significantly improved level of sensitivity is achieved. Reference to "critical annealing temperature" ("Tc") should be understood as a reference to the highest annealing temperature at which an amplification reaction, such as PCR, operates at optimal efficiency with respect to amplifying the desired target. The efficiency of operation of amplification can be assessed by the Ct. Specifically, the optimal amplification at each cycle of the PCR depends on optimal hybridisation of each primer to the target molecules such that effectively all target molecules become hybridised. Without limiting the present invention to any one theory or mode of action, if a series of amplification reactions are performed using a range of different but progressively increasing annealing temperatures, there will be identified a temperature at which hybridisation becomes incomplete, amplification becomes inefficient and the Ct increases. The highest temperature before which these amplification inefficiencies become evident is the critical annealing temperature (Tc), as is illustrated in FIG. 3. It will be well understood by the person skilled in the art that the Tc for a primer is an empirically determined temperature that it will differ from the calculated Tm by several degrees. The magnitude of this difference will vary from primer to primer. Still further, since the precise value of the Tc will depend on the amplification conditions and on the resolution of the temperature gradient produced by the instrument used for determining the Tc, the skilled person will appreciate that amplification conditions under which the Tc is calculated should correspond to the amplification conditions which are thereafter used for the amplification of the test samples. Determination of the Tc value is well within the skill of the person in the art and can be performed by any suitable means, such as using an instrument which enables a series of real-time amplifications of target DNA over a range of annealing temperatures. An example of Tc determination is described in Example 2.

It should also be appreciated that the determination of Tc is required to be assessed in the context of the specific primers which are proposed to be used to amplify the test sample since its utility is linked to an analysis of the actual performance of the primers selected. Accordingly, this analysis will be required to be completed before the method of the invention is applied and will be required to be performed in the context of each different set of primers proposed to be utilised. However, as detailed above, methods for determining Tc are well known and can be routinely and easily performed without any undue burden. To this end, reference to the annealing temperature being selected relative to the Tc "of the subject reaction" should be understood as a reference to the fact that the relevant Tc is that of the particular primers which are sought to be used in the context of a given reaction. The Tc is therefore not a fixed value which can be applied across a range of different primer sets.

Reference to "annealing temperature" should be understood as a reference to the temperature of the phase of amplification during which hybridisation of the primers to the target nucleic acid region (template) occurs. As detailed hereinbefore, one aspect of the present invention is based on the determination that reduced non-specific amplification can be achieved if the annealing temperature which is used falls between the Tc and 3° C. below the Tc (herein referred to as "Tc-3° C."). The annealing temperature of the method of the present invention is therefore likely to vary from one reaction to another when the primers which are used differ. This design is entirely unlike most amplification systems where a fixed annealing temperature is used across all reaction. It should be further understood that reference to the annealing temperature falling "within" or "between" the Tc and (Tc-3° C.) includes selecting to use the Tc or the (Tc-3° C.) temperatures themselves. It should also be understood that the use of temperatures at or about the outer limits of this range are also contemplated, such as temperatures slightly below or above these limits but which function equivalently to the temperatures at or within this range.

It would be further appreciated that since the forward and reverse primers have different sequences, the Tc of the two primers within a single reaction may vary somewhat. The ASO primer is the most important primer in terms of minimising nonspecificity and, in practice, the same reverse consensus (usually J) primer will often be used in association with different ASO primers when studying samples from different patients. In this situation, the skilled person would appreciate that the reverse primer may be designed first, aiming at a particular Tm, and that its Tc can then be then determined experimentally. The ASO primer is thereafter designed, aiming at a Tm 1-2° C. less than that of the reverse primer. The Tc of the ASO primer should then be slightly below the Tc of the reverse primer and if the annealing temperature of the PCR is based on the Tc of the ASO primer then the specificity of the PCR will be optimised.

As detailed hereinbefore, the forward primer is usually the ASO primer, being directed to the most variable region of the IgH or TCR rearrangement, and the reverse primer is directed to a downstream gene segment of the IgH or TCR gene. Since the improved sensitivity afforded by the present invention results from reduced non-specificity, it is advantageous to also design the non-ASO primers as hereinbefore described in order to further minimise non-specificity.

As hereinbefore described, in a further aspect the skilled person may seek to design and synthesise the primer to enable optimal hybridisation, such as by inserting one or more A and/or T nucleotides at the 3' end of the primer. In one embodiment, where two or more A and/or T nucleotides are utilised, these are positioned directly adjacent to one another. That is, in sequence. Specifically, one may preferably include at least one A or T nucleotide at the 3' terminal nucleotide position of either or both of the forward or reverse primers. In another example, said A or T nucleotide is included at the 3' terminal nucleotide position of the reverse primer alone, at the 3' terminal nucleotide position of of the J primer or in any of the J primers which are disclosed in Table 1. In another embodiment, there is an A and/or T nucleotide at each of the two most 3' terminal nucleotide positions of the primer. In still another embodiment there is an A and/or T nucleotide at each of the three most 3' terminal nucleotide positions of the primer. In yet another embodiment there is an A and/or T nucleotide at each of the four most 3' terminal nucleotide positions of the primer. In still yet another embodiment there is an A and/or T nucleotide at each of the five most 3' terminal nucleotide positions of the primer. In yet still another embodiment there is an A and/or T nucleotide at each of the six most 3' terminal nucleotide positions of the primer. Reference to the "3' terminal end" of the primer should be understood as a reference to the end of the primer which will undergo extension if it hybridises to its target. The one, two, three, four, five or six nucleotides which are referred to within this context are therefore the terminal nucleotides of the primer, at the 3' end, prior to the primer undergoing any extension. Any combination of A or T nucleotides may be used at any one of more of these positions.

In one embodiment there is an A or T nucleotide at the 3' terminal nucleotide position of the primer. In another embodiment there is an A and/or T nucleotide at each of the two most 3' terminal nucleotide positions of the primer. In still another embodiment there is an A and/or T nucleotide at each of the three most 3' terminal nucleotide positions of the primer. In yet another embodiment there is an A and/or T nucleotide at each of the four most 3' terminal nucleotide positions of the primer. In still yet another embodiment there is an A and/or T nucleotide at each of the five most 3' terminal nucleotide positions of the primer. In yet still another embodiment there is an A and/or T nucleotide at each of the six most 3' terminal nucleotide positions of the primer.

As detailed hereinbefore, still further sensitivity can be achieved if the amplification is designed to incorporate a melting curve analysis. Reference to "melting curve analysis" should be understood as a reference to the analysis of the melting point of an amplicon as a means to identify non-specific amplification. Since the melting point of an amplicon is linked to the composition and length of the nucleotide sequence of the amplicon, melting curve analysis may be used to detect length and/or sequence variation within samples and, in particular to distinguish the generation of specific amplicons from non-specific amplicons. Means for performing melting curve analysis following completion of the PCR are well known to those skilled in the art and are routinely incorporated into amplification reactions. Any suitable method may be utilised, such as incorporating into the reaction molecules which fluoresce, or are otherwise detectable, when they bind non-specifically to DNA duplexes. Without limiting the present invention to any one theory or mode of action, if a melting curve analysis is performed by slowly raising the temperature, fluorescence decreases progressively over a wide range of temperature owing to melting of a heterogeneous range of DNA duplexes. The presence of a homogeneous subpopulation of duplexes, such as the target amplicons, can be recognised by a sudden decrease in fluorescence over a narrow temperature range. This is most easily recognised by following the first derivative i.e. slope, of the fluorescence vs temperature. A peak at a specific temperature will be observed. Nonspecific amplification typically does not produce a peak, or produces a complex pattern or produces a peak at a different temperature to that of the target amplicon.

Figure 4:
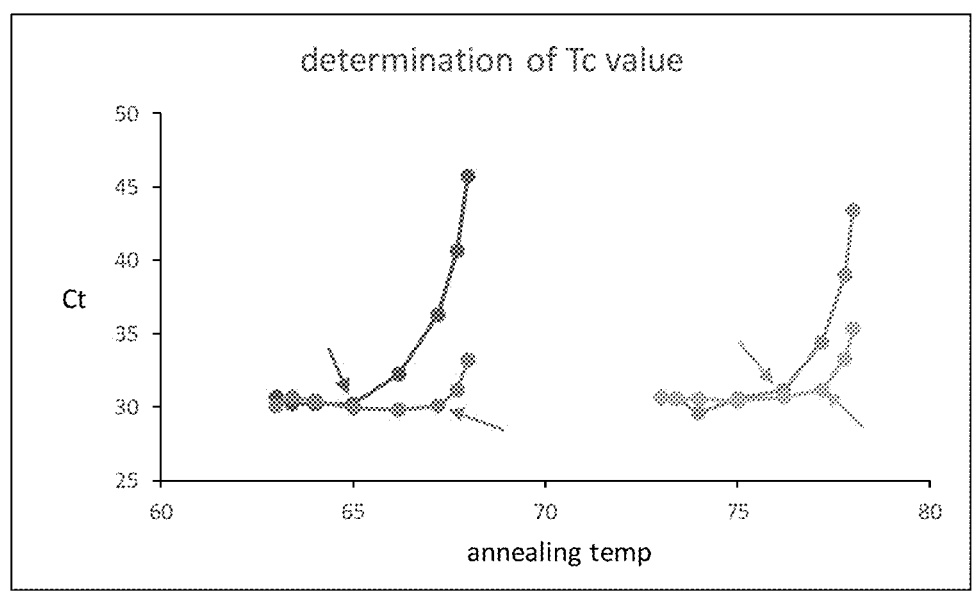
FIG. 4 is a graphical representation of the method for determining the critical annealing temperature (Tc). A series of PCR's is performed using a range of annealing temperatures. The Tc is the highest temperature at which the PCR maintains optimum efficiency as shown by the maintenance of the minimum Ct. Four different ASO primers were tested and the Tc for each is indicated by the arrow.
Figure 5:
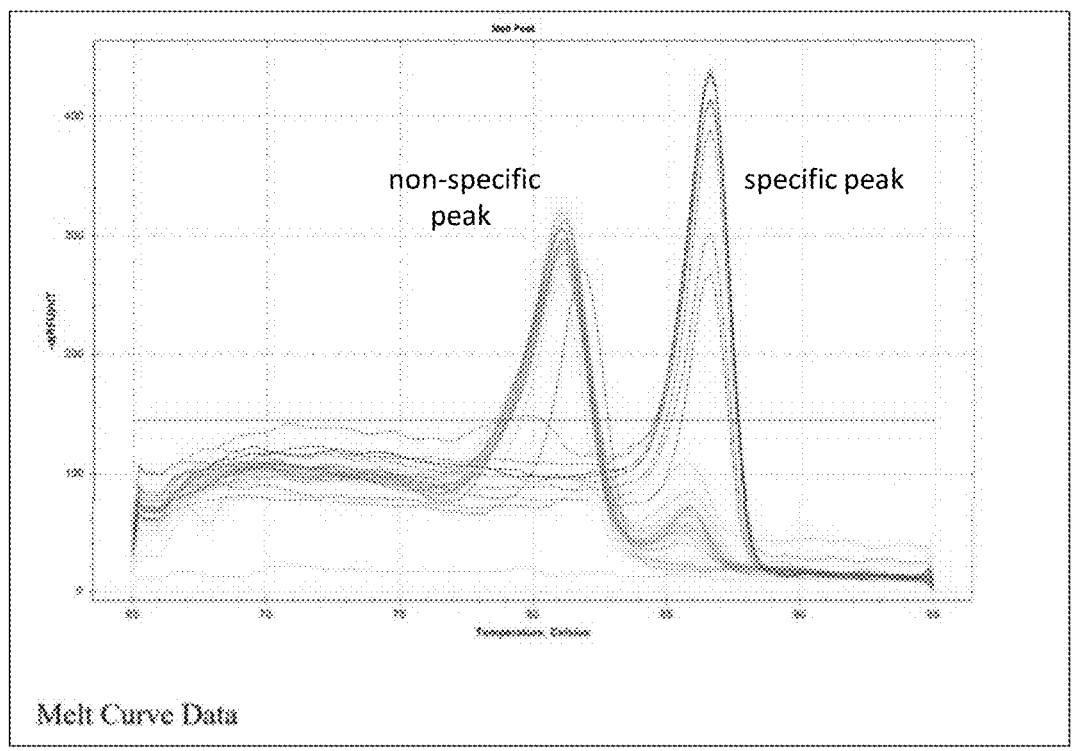
FIG. 5 shows the results of a melting curve analysis. The PCR contained both the probe, for measurement of the Ct, and a low concentration of the fluorescent dye Syto 82. At the end of the PCR the temperature was slowly raised and fluorescence was continuously measured. The figure shows the first derivative of the fluorescence vs temperature curve and the separate peaks for non-specific amplification and specific amplification are evident.
Figure 6:
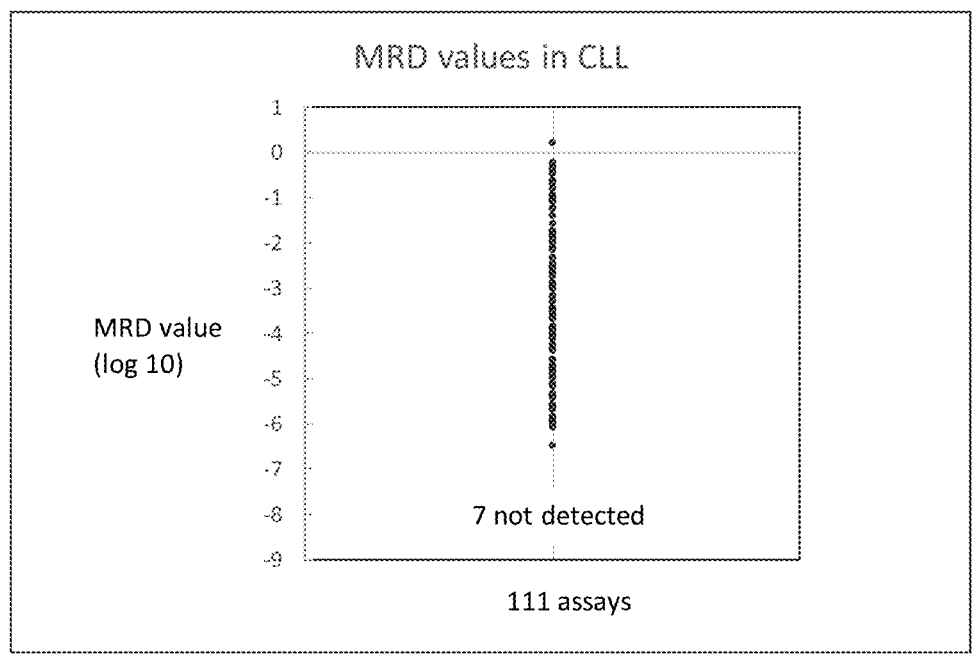
FIG. 6 shows the results of measurements of MRD in 111 samples from 36 patients with chronic lymphocytic leukemia during treatment. Sensitivity of $<10^{-6}$ was achieved.

Still further, the incorporation into the method of the invention of a probe coupled to a detection means provides still further specificity since the sequence of the probe is complementary to the sequence of the target amplicon, thereby binding almost entirely to its intended target. Molecules which fluoresce when they bind non-specifically to DNA duplexes have been used for end-point Ct measurement in the PCR but are contraindicated for this purpose in the present method as they bind to all DNA duplexes and their Ct value is unreliable when attempting to measure low levels of MRD. Such fluorophores are therefore recommended to be used for the melting curve analysis only. However, such fluorophore molecules can be used in the present method for melting point analysis of DNA duplexes present after completion of the PCR, providing that the nature and concentration of the particular fluorophore used are such as to not affect the efficiency of PCR amplification as shown by lack of an effect on the Ct value provided by the probe. An example of melting curve analysis using the fluorophore Syto 82 to distinguish specific amplification from nonspecific amplification is shown in FIG. 4

The probe therefore provides the Ct and the dye, or other suitable means, enables melting analysis. It would be appreciated by the skilled person that the probe can be designed to be coupled with any suitable detection means. In the context of the methods exemplified herein, however, both the probe and dye fluoresce in response to UV but their emission spectra differ so they can be separately monitored.

Accordingly, in yet another embodiment, said method includes Ct determination, preferably using a probe which is directed to the rearranged Ig or TCR of interest, which probe is coupled to a detection means.

The method of the present invention is particularly useful in the context of improving the sensitivity of detection of rearrangements of the Ig or TCR gene which comprise just one N region (also alternatively termed "gene segments" in this specification). Without limiting the present invention to any one theory or mode of action, a complete Ig heavy chain gene rearrangement or a complete TCR β chain gene rearrangement, which both comprise a VDJ rearrangement, will usually include two N regions (N1 and N2). However, a partial rearrangement may comprise either one or two N regions depending on whether one or more of the V, D or J gene segments exhibit internal N regions which form during the rearrangement process. The Ig light chain and the TCR α chain, for example, comprise only a VJ rearrangement, while a partial DJ rearrangement of the IgH chain and TCR β chain occurs prior to the completion of the rearrangement of a V gene segment with the DJ recombination. Accordingly, a VDJ rearrangement will generate two N regions (occasionally more than two if N regions within the V, D or J gene segments are generated), these being configured as $VN_1DN_2J$, while the Ig light chain, TCR α chain or the transient partial rearrangements may generate only one N region, such as VNJ or DNJ. This may apply, for example, to genetic loci such as IGκ and TCRγ which do not contain D genes and the rearrangement involves only the V and J genes. This may also apply to rearrangements of the IGH or TCRβ genes where there is only a "partial" rearrangement which may have a VJ or DJ structure and only one N region.

In another aspect there is therefore provided a method of amplifying an Ig or TCR nucleic acid region which is characterised by the rearrangement of two or more V, D or J gene segments, which rearrangement is characterised by only one N region, said method comprising contacting a nucleic acid sample of interest with forward and reverse primers directed to said rearranged Ig or TCR nucleic acid region and amplifying said nucleic acid sample using:

(i) an annealing temperature within the range between Tc and (Tc-3° C.) of the subject amplification reaction; and/or (ii) at least one primer which comprises at least one A and/or T nucleotide at the 3' terminal nucleotide position of said primer;

and optionally a means to conduct a melting curve analysis.

In one embodiment, said at least one primer is the ASO primer.

In another embodiment, said method comprises using both an annealing temperature within the range between Tc and (Tc-3° C.) of the subject amplification reaction and at least one primer which comprise an A or T nucleotide at the 3' terminal nucleotide position of said primer.

In still another embodiment, said nucleic acid is DNA.

In yet another embodiment there is an A and/or T nucleotide at each of the two most 3' terminal nucleotide positions of said primer. In still another embodiment there is an A and/or T nucleotide at each of the three most 3' terminal nucleotide positions of said primer. In yet another embodiment there is an A and/or T nucleotide at each of the four most 3' terminal nucleotide positions of the primer. In still yet another embodiment there is an A and/or T nucleotide at each of the five most 3' terminal nucleotide positions of the primer. In yet still another embodiment there is an A and/or T nucleotide at each of the six most 3' terminal nucleotide positions of the primer.

In still yet another embodiment a melting curve analysis is performed.

In yet still another embodiment, said method includes Ct determination, preferably using a probe which is directed to the rearranged Ig or TCR of interest, which probe is coupled to a detection means.

In yet still another embodiment, said primer directed to the downstream gene segment is directed to the J segment.

Examples of J primers suitable for use in the context of this embodiment of the present invention are provided in Table 1, below.

TABLE 1

J primers used for IGH and TCRβ. These are the longest primers used for these regions. Shorter primers are also used and comprise the same middle and 3' ends of the above primers but with a variable number of 5' bases removed in order to result in a primer with the desired Tm.

| name | sequence | Tm | Tc | SEQ ID NO |
|---|---|---|---|---|
| IGH | | | | |
| AAMJ1b | ctttgctgagcacctgtccccaagtctgaa | 73.2 | 75.8 | SEQ ID NO: 1 |
| AAMJ2 | aggccggctgcagaccccagata | 74 | 78.8 | SEQ ID NO: 2 |
| AAMJ3c | cccccggacattatctcccagctcca | 72.9 | 76.6 | SEQ ID NO: 3 |
| AAMJ4c | gcttatttccccccaaaaatgcagcaaaaccctt | 73.4 | 76.6 | SEQ ID NO: 4 |
| AAMJ5c | cctccaaaatgcctccaagactctgaccctga | 73.5 | 77.6 | SEQ ID NO: 5 |
| AAMJ6c | aggaaacccacaggcagtagcagaaaacaa | 73.3 | 77.0 | SEQ ID NO: 6 |
| TCRβ | | | | |
| TCR1.1b | ttccctgtgacggatctgcaaaagaacctga | 72.8 | | SEQ ID NO: 7 |
| TCR1.2b | ccctcctagagaccccagccttacctacaa | 73.6 | | SEQ ID NO: 8 |
| TCR1.3b | caagttcccagctgtccagccttgacttact | 72.7 | | SEQ ID NO: 9 |
| TCR1.4b | ccaggaactccgaccttatgatacactatcccgaaagaa | 72.9 | | SEQ ID NO: 10 |
| TCR1.5b | atggccataccaccctgattctgcaacttaccta | 73.3 | | SEQ ID NO: 11 |
| TCR1.6b | gagtcaagagtggagcccccatacctgt | 72.4 | | SEQ ID NO: 12 |
| TCR2.1b | cacctggagccccttcttacctagca | 72.6 | | SEQ ID NO: 13 |
| TCR2.2b | cggagccccaaccgcctcctt | 73.6 | | SEQ ID NO: 14 |
| TCR2.3b | ggagcccgcttaccgagcact | 72.9 | | SEQ ID NO: 15 |
| TCR2.4b | ccggcggccccagctt | 71.6 | | SEQ ID NO: 16 |
| TCR2.5b | gcgctcaccgagcaccagga | 71.8 | | SEQ ID NO: 17 |
| TCR2.5c | ccgcgctcaccgagcaccagga | 71.6 | | SEQ ID NO: 18 |
| TCR2.5d | cccgcgctcaccgagcaccagga | 71.6 | | SEQ ID NO: 19 |
| TCR2.6b | cgcgaaaactcacccagcacggtca | 73.1 | | SEQ ID NO: 20 |
| TCR2.7d | ggaaggtggggagacgcccgaat | 72.6 | | SEQ ID NO: 21 |

In accordance with the embodiments of the present invention herein described, one may design the primers to hybridise to one or more N gene segments, such as the $N_1$ gene segment 5' to the D gene segment, the $N_2$ gene segment 3' to the D gene segment of a fully rearranged VDJ gene or the N regions (gene segments) which may be formed within a rearranged V, D or J gene segment. In this regard, in one embodiment, a high level of sensitivity is achieved where that at least one of the forward or reverse primers hybridises to at least two N gene segments. In a preferred embodiment, it is the forward (ASO) primer which hybridises to the two N gene segments. In this embodiment, the reverse primer may hybridise to a downstream gene segment, such as the J gene segment and need not even necessarily be patient specific. In another embodiment, it is the reverse primer which hybridises to the at least two N gene segments.

It should also be recognised that there will be situations in which it is preferable that the primer be directed towards only one N region despite the VDJ rearrangement containing two or more N regions. Such a situation may arise if the N region being targeted is particularly long and thus enables high specificity, or the N region being targeted contains a sufficient number of A or T bases to enable the 3' end of the primer to comprise the complementary T or A bases, or if an N region not to be targeted contains an insufficient number of A or T bases.

To the extent that one is seeking to design a primer to hybridise across two N gene segments, the design of the primers of the present invention is such that in order to hybridise across two N gene segments which are both positioned at the junctions of V, D or J gene segments, the primers must hybridise across at least three consecutive gene segments of the recombined gene of interest wherein the 5' and 3' gene segments of these three consecutive gene segments are the N regions/gene segments. Accordingly, the primer is structured such that it comprises three subregions which are each designed to hybridise to one of the three consecutive gene segments of the recombined gene of interest, two of which are N gene segments. By "consecutive" is meant that the three gene segments have been recombined such that they are directly adjacent to one another, preferably in a linear arrangement. In this regard, it should be understood that each of the three subregions of the primer which hybridise to the three recombined and consecutive gene segments are operably linked to one another to form a single primer.

The primer subregions may be the same or different in terms of length. It should be understood that depending on the length of each of these oligonucleotide subregions and the specific gene segment target to which they are directed, they may exclusively hybridise to all or part of just one gene segment or they may hybridise to all or part of each of a number of gene segments. Conceptually, a primer to a partial rearrangement (DNJ or VNJ) may be designed to hybridise, for example, to one of the following rearranged gene segment targets: N, DN, NJ, DNJ, VN, NJ, VNJ. A primer to a complete $VN_1DN_2J$ rearrangement may be designed to hybridise, for example, to one of the following rearranged gene segment targets: $N_1$, $VN_1$, $N_1D$, $VN_1D$, $N_1DN_2$, $VN_1DN_2$, $N_1DN_2J$, $VN_1DN_2J$, $N_2$, $DN_2$, $N_2J$, $DN_2J$. It should be understood that the V, D and J gene segments may also comprise an N region within that segment itself.

As would be appreciated, when the primer is designed to hybridise to two N gene segments the primer will span the full length of the gene segment intervening the two N gene segments. The usual context is a VDJ rearrangement and the intervening gene segment is usually the D gene segment. It would be appreciated by the person of skill in the art that due to the length of the D gene segment, designing a primer which hybridises across the full length of the D gene segment can result in a loss of specificity due to the fact that the subregion of the primer which hybridises to the D gene segment is likely to represent the longest subregion of the primer, since the N gene segments are usually relatively short. The specificity for the N gene segments may therefore be compromised since most of the hybridisation of the primer will be determined by its complementarity to the D gene segment. Since the specific D gene segment of interest is likely to be found in many other VDJ rearrangement combinations, in addition to unrearranged genes, it will therefore be detectable in many different cells other than just the cell of interest. This can result in significant false positive results. To reduce the incidence of this non-specific binding (regardless of how many N regions the primer is directed to), modifications can be made to the subregion of the primer which hybridises to the D gene segment, in order to reduce its specificity. Methods of achieving this include, but are not limited to:

(i) The introduction of one or more spacers or linkers to the subregion of the primer which is designed to hybridise to the D gene segment (or other gene segment to which specificity is sought to be reduced) to decrease hybridisation of that subregion of the oligonucleotide to the D gene segment.

(ii) Synthesis of the primer such that at a number of nucleotide positions within the subregion of the primer which is designed to hybridise to the gene segment, such as the D gene segment, the addition of a single nucleotide is replaced by the addition of a nucleotide randomly selected from an equimolar mixture of all 4 nucleic acid bases (referred to as an N mixture). This significantly reduces the contribution of hydrogen bonding at these positions to the overall hybridisation of the oligonucleotide primer since with each round of amplification at the substituted position there is only a 1 in 4 probability of appropriate bonding between the template nucleotide and the oligonucleotide nucleotide. The use of a less random N mixture e.g. only A/T, has a lesser effect. Without limiting the present invention to any one theory or mode of action, it has been determined that modifying with an N mixture either approximately every fourth base or a string of 3-7 adjacent nucleotides of a primer subregion which is directed to a lengthy gene segment can achieve a sufficient reduction in specificity but without the loss of primer functionality.

Facilitating the interaction of the primer of the present invention with the target DNA may be performed by any suitable method. Those methods will be known to those skilled in the art. Methods for achieving primer directed amplification are also very well known to those of skill in the art. In one method, said amplification is polymerase chain reaction, NASBA or strand displacement amplification. Preferably, said amplification is polymerase chain reaction.

Reference to a "sample" should be understood as a reference to either a biological or a non-biological sample. Examples of non-biological samples includes, for example, the nucleic acid products of synthetically produced nucleic acid populations. Reference to a "biological sample" should be understood as a reference to any sample of biological material derived from a mammal or mammalian tissue culture such as, but not limited to, cellular material, blood, mucus, faeces, urine, tissue biopsy specimens or fluid which has been introduced into the body of an animal and subsequently removed (such as, for example, the saline solution extracted from the lung following lung lavage or the solution retrieved from an enema wash). The biological sample which is tested according to the method of the present invention may be tested directly or may require some form of treatment prior to testing. For example, a biopsy sample may require homogenisation prior to testing. Further, to the extent that the biological sample is not in liquid form it may require the addition of a reagent, such as a buffer, to mobilise the sample.

To the extent that the target DNA is present in a biological sample, the biological sample may be directly tested or else all or some of the nucleic acid material present in the biological sample may be isolated prior to testing. It is within the scope of the present invention for the target nucleic acid molecule to be pre-treated prior to testing, for example inactivation of live virus or being run on a gel. It should also be understood that the biological sample may be freshly harvested or it may have been stored (for example by freezing) prior to testing or otherwise treated prior to testing (such as by undergoing culturing).

Reference to "contacting" the sample with the primer should be understood as a reference to facilitating the mixing of the primer with the sample such that interaction (for example, hybridisation) can occur. Means of achieving this objective would be well known to those of skill in the art.

The choice of what type of sample is most suitable for testing in accordance with the method disclosed herein will be dependent on the nature of the situation, such as the nature of the condition being monitored. For example, in a preferred embodiment a neoplastic condition is the subject of analysis. If the neoplastic condition is a lymphoid leukaemia, a blood sample, lymph fluid sample or bone marrow aspirate would likely provide a suitable testing sample. Where the neoplastic condition is a lymphoma, a lymph node biopsy or a blood or marrow sample would likely provide a suitable source of tissue for testing. Consideration would also be required as to whether one is monitoring the original source of the neoplastic cells or whether the presence of metastases or other forms of spreading of the neoplasia from the point of origin is to be monitored. In this regard, it may be desirable to harvest and test a number of different samples from any one mammal. Choosing an appropriate sample for any given detection scenario would fall within the skills of the person of ordinary skill in the art.

The term "mammal" to the extent that it is used herein includes humans, primates, livestock animals (e.g. horses, cattle, sheep, pigs, donkeys), laboratory test animals (e.g. mice, rats, rabbits, guinea pigs), companion animals (e.g. dogs, cats) and captive wild animals (e.g. kangaroos, deer, foxes). preferably, the mammal is a human or a laboratory test animal. Even more preferably the mammal is a human.

The method of this aspect of the present invention provides a means for both detecting the presence of a target nucleic acid region of interest (such as for diagnostic or monitoring purposes) and, optionally, quantifying and/or isolating that target. Accordingly, one is provided with means of detecting, enriching or purifying a target nucleic acid population of interest for any purpose, such as further analysis of the target.

Another aspect of the present invention provides a method of detecting and/or monitoring a clonal population of cells in a mammal, which clonal cells are characterised by an Ig or TCR nucleic acid region which is characterised by the rearrangement of two or more V, D or J gene segments, said method comprising:
(i) contacting the DNA material of a biological sample derived from a mammal with the forward and reverse primers as hereinbefore defined for a time and under conditions sufficient to facilitate interaction of said primers with said target nucleic acid molecule;
(ii) amplifying said nucleic acid target using (a) an annealing temperature within the range between Tc and (Tc-3° C.) of the subject amplification reaction; and/or (b) at least one primer which comprises at least one A and/or T nucleotide at the 3' terminal nucleotide position of said primer n; and optionally a means to conduct a melting curve analysis; and
(iii) detecting said amplified product.

In one embodiment, said at least one primer is the ASO primer.

In another embodiment, said method comprises using both an annealing temperature within the range between Tc and (Tc-3° C.) of the subject amplification reaction and one or more primers which comprise an A or T nucleotide at the 3' terminal nucleotide position of said primer.

In still another embodiment, said nucleic acid is DNA.

In yet another embodiment there is an A and/or T nucleotide at each of the two most 3' terminal nucleotide positions of said primer. In still another embodiment there is an A and/or T nucleotide at each of the three most 3' terminal nucleotide positions of said primer. In yet another embodiment there is an A and/or T nucleotide at each of the four most 3' terminal nucleotide positions of the primer. In still yet another embodiment there is an A and/or T nucleotide at each of the five most 3' terminal nucleotide positions of the primer. In yet still another embodiment there is an A and/or T nucleotide at each of the six most 3' terminal nucleotide positions of the primer.

In still yet another embodiment a melting curve analysis is performed.

In yet still another embodiment, said method includes Ct determination, preferably using a probe which is directed to the rearranged Ig or TCR of interest, which probe is coupled to a detection means.

In a further embodiment, said amplification reaction is polymerase chain reaction.

In yet still another embodiment, said primer directed to the downstream gene segment is directed to the J segment.

Reference to "cells" should be understood as a reference to all forms of cells from any species and to mutants or variants thereof. Preferably, the cell is a lymphoid cell, although the method of the present invention can be performed on any type of cell which may have undergone a partial or full Ig or TCR rearrangement. Without limiting the present invention to any one theory or mode of action, a cell may constitute an organism (in the case of unicellular organisms) or it may be a subunit of a multicellular organism in which individual cells may be more or less specialised (differentiated) for particular functions. All living organisms are composed of one or more cells. The subject cell may form part of the biological sample which is the subject of testing in a syngeneic, allogeneic or xenogeneic context. A syngeneic context means that the clonal cell population and the biological sample within which that clonal population exists share the same MHC genotype. This will most likely be the case where one is screening for the existence of a neoplasia in an individual, for example. An "allogeneic" context is where the subject clonal population in fact expresses a different MHC to that of the individual from which the biological sample is harvested. This may occur, for example, where one is screening for the proliferation of a transplanted donor cell population (such as an immunocompetent bone marrow transplant) in the context of a condition such as graft versus host disease. A "xenogeneic" context is where the subject clonal cells are of an entirely different species to that of the subject from which the biological sample is derived. This may occur, for example, where a potentially neoplastic donor population is derived from xenogeneic transplant.

"Variants" of the subject cells include, but are not limited to, cells exhibiting some but not all of the morphological or phenotypic features or functional activities of the cell of which it is a variant. "Mutants" includes, but is not limited to, cells which have been naturally or non-naturally modified such as cells which are genetically modified.

By "clonal" is meant that the subject population of cells has derived from a common cellular origin. For example, a population of neoplastic cells is derived from a single cell which has undergone transformation at a particular stage of differentiation. In this regard, a neoplastic cell which undergoes further nuclear rearrangement or mutation to produce a genetically distinct population of neoplastic cells is also a "clonal" population of cells, albeit a distinct clonal population of cells. In another example, a T or B lymphocyte which expands in response to an acute or chronic infection or immune stimulation is also a "clonal" population of cells within the definition provided herewith. In yet another example, the clonal population of cells is a clonal microorganism population, such as a drug resistant clone which has arisen within a larger microorganismal population. Preferably, the subject clonal population of cells is a neoplastic population of cells or a clonal immune cell population.

In one embodiment, said clonal cells are a population of clonal lymphoid cells.

It should be understood that reference to "lymphoid cell" is a reference to any cell which has rearranged at least one germ line set of immunoglobulin or TCR variable region gene segments. The immunoglobulin variable region encoding genomic DNA which may be rearranged includes the variable regions associated with the heavy chain or the κ or λ light chain while the TCR chain variable region encoding genomic DNA which may be rearranged include the α, β, γ and δ chains. In this regard, a cell should be understood to fall within the scope of the "lymphoid cell" definition provided the cell has rearranged the variable region encoding DNA of at least one immunoglobulin or TCR gene segment region. It is not necessary that the cell is also transcribing and translating the rearranged DNA. In this regard, "lymphoid cell" includes within its scope, but is in no way limited to, immature T and B cells which have rearranged the TCR or immunoglobulin variable region gene segments but which are not yet expressing the rearranged chain (such as TCR-thymocytes) or which have not yet rearranged both chains of their TCR or immunoglobulin variable region gene segments. This definition further extends to lymphoid-like cells which have undergone at least some TCR or immunoglobulin variable region rearrangement but which cell may not otherwise exhibit all the phenotypic or functional characteristics traditionally associated with a mature T cell or B cell. Accordingly, the method of the present invention can be used to monitor neoplasias of cells including, but not limited to, lymphoid cells at any differentiative stage of development, activated lymphoid cells or non-lymphoid/lymphoid-like cells provided that rearrangement of at least part of one variable region gene region has occurred. It can also be used to monitor the clonal expansion which occurs in response to a specific antigen.

With respect to this aspect of the present invention, reference to "monitoring" should be understood as a reference to testing the subject for the presence or level of the subject clonal population of cells after initial diagnosis of the existence of said population. "Monitoring" includes reference to conducting both isolated one-off tests or a series of tests over a period of days, weeks, months or years. The tests may be conducted for any number of reasons including, but not limited to, predicting the likelihood that a mammal which is in remission will relapse, screening for minimal residual disease, monitoring the effectiveness of a treatment protocol, checking the status of a patient who is in remission, monitoring the progress of a condition prior to or subsequently to the application of a treatment regime, in order to assist in reaching a decision with respect to suitable treatment or in order to test new forms of treatment. The method of the present invention is therefore useful as both a clinical tool and a research tool.

It should also be understood that although it is preferable that the rearrangement of at least one variable region gene region has been completed, the method of the present invention is nevertheless applicable to monitoring neoplastic cells which exhibit only partial rearrangement. For example, a B cell which has only undergone the DJ recombination event is a cell which has undergone only partial rearrangement. Complete rearrangement will not be achieved until the DJ recombination segment has further recombined with a V segment. The method of the present invention can therefore be designed to detect the partial or complete variable region rearrangement of one TCR or immunoglobulin chain utilising a reference molecule complementary to this marker sequence or, for example, if greater specificity is required and the neoplastic cell has rearranged the variable region of both TCR or immunoglobulin chains, primer molecules directed to both forms of rearrangement can be utilised.

Reference to a "neoplastic cell" should be understood as a reference to a cell exhibiting abnormal "growth". The term "growth" should be understood in its broadest sense and includes reference to proliferation. In this regard, an example of abnormal cell growth is the uncontrolled proliferation of a cell. The uncontrolled proliferation of a lymphoid cell may lead to a population of cells which take the form of either a solid tumour or a single cell suspension (such as is observed, for example, in the blood of a leukemic patient). A neoplastic cell may be a benign cell or a malignant cell. In a preferred embodiment, the neoplastic cell is a malignant cell. In this regard, reference to a "neoplastic condition" is a reference to the existence of neoplastic cells in the subject mammal. Although "neoplastic lymphoid condition" includes reference to disease conditions which are characterised by reference to the presence of abnormally high numbers of neoplastic cells such as occurs in leukemias, lymphomas and myelomas, this phrase should also be understood to include reference to the circumstance where the number of neoplastic cells found in a mammal falls below the threshold which is usually regarded as demarcating the shift of a mammal from an evident disease state to a remission state or vice versa (the cell number which is present during remission is often referred to as the "minimal residual disease"). Still further, even where the number of neoplastic cells present in a mammal falls below the threshold detectable by the screening methods utilised prior to the advent of the present invention, the mammal is nevertheless regarded as exhibiting a "neoplastic condition".

Disease conditions suitable for analysis in this regard are any lymphoid malignancies such as acute lymphoblastic leukaemia, chronic lymphocytic leukaemia, lymphoma and myeloma. Monitoring of minimal residual disease is of importance in all of these conditions.

Preferably, said condition is a neoplasia and even more preferably a lymphoid neoplasia.

In one particular embodiment, the method of the present invention is used to detect minimum residual disease in the context of lymphoid leukaemias.

Yet another aspect of the present invention is directed to an isolated primer as hereinbefore described.

Yet still another aspect of the present invention is directed to a kit for facilitating the identification of an Ig or TCR nucleic acid region which is characterised by the rearrangement of two or more V, D or J gene segments, said kit comprising compartments adapted to contain any one or more of the oligonucleotide primers as hereinbefore defined, reagents useful for facilitating interaction of said primer with the target nucleic acid molecule and reagents useful for enabling said interaction to result in amplification of said nucleic acid target. Further compartments may also be included, for example, to receive biological or non-biological samples.

Further features of the present invention are more fully described in the following non-limiting examples.

Example 1

Guidelines for Primer Design

The 3' End
the last 3' base to be an A/T
preferably the last two or even three bases to be A/T
can have A/T as the base for up to the last four most 3' bases. If more than this there is the risk that the primer will not perform as efficiently.
at least 2 G/C in the last 7 bases.
Design if using 2 N Regions
the primer will be directed to part or all of N1, all of D, and part or all of N2.
It may be advantageous to include up to 4 bases 5' to N1 and/or 1-3 bases 3' to N2. This takes advantage of the semi-unique V-N1 and N2-J junctions and any A/T bases offered by J.

If the Tm of the primer is too high, greater than 74° C., one or more N bases can be inserted into the D region to lower the effective Tm.

Design if using one N Region

Only one N region will be available in the presence of V-N-J or a partial D-N-J rearrangement. Sometimes, even if 2 N regions are available, it may be decided to use only one, particularly if it is long, comprises a favourable heterogeneous sequence of bases and enables a good 3' end to be designed. When the N region is short and/or it is difficult to design a primer with a good 3' end:

- If the N region is followed by a D region, it is usually advantageous to extend the primer 4-6 bases into the D region, particularly if this improves the 3' end. This takes advantage of the semi-unique N-D junction.
- If the N region is followed by the J region, it is usually advantageous to extend the primer 1-3 bases into the J region, occasionally further if one is searching for A/T at the 3' end. However, particularly in this situation, it is important to test several different primers.
- If the N region is preceded by the 3' end of the V region then, provided the primer does not become too long, it may be advantageous to incorporate 3 to 5 bases of V into the 5' end. This takes advantage of the semi-unique V-N junction.

Tm and Annealing Temperature

The length and Tm of the ASO primer depend on the nature of the rearrangement but in many cases there is some flexibility in deciding on the precise length and Tm. If so, it is recommended to design the primer so that its Tm is approximately the same or one ° C. less than the Tm of the reverse primer.

The annealing temperature for use in the PCR depends on the Tm of the primer.

Guidelines are

Tm=59-61, annealing temperature=63-64
Tm=69-71, annealing temperature=72.
Tm=71-74, annealing temperature=75
Tm>74, annealing temperature=75 but consider the use of N bases to decrease Tm.

These guidelines usually result in the annealing temperature being within three ° C. of the Tc value. However, some difficulty may be anticipated for primers for rearrangements with only one N region, particularly if the N region contains 5 or fewer bases. For such rearrangements the annealing temperature should be close to or at the Tc value in order to produce minimal or no nonspecificity. It is also wise to synthesise and test several candidate primers.

Note

The above are only guidelines and reliance should be placed on the temperature gradient results and the primer sequence. For some patients it is advisable to synthesise and test more than one candidate primer.

Example 2

Different Sets of J Primers Used for IGH Rearrangements

The usual set used is either AAM or setB.

| name | Tm | Tc | primer sequence |
|---|---|---|---|
| AAMJ1b | 73.2 | 75.8 | CTTTGCTGAGCACCTGTCCCCAAGTCTGAA |
| AAMJ2 | 74 | 78.8 | AGGCCGGCTGCAGACCCCAGATA |
| AAMJ3c | 72.9 | 76.6 | CCCCCGGACATTATCTCCCAGCTCCA |
| AAMJ4c | 73.4 | 76.6 | GCTTATTTCCCCCCAAAAATGCAGCAAAACCCTT |
| AAMJ5c | 73.5 | 77.6 | CCTCCAAAATGCCTCCAAGACTCTGACCCTGA |
| AAMJ6c | 73.3 | 77 | AGGAAACCCCACAGGCAGTAGCAGAAAACAA |
| Jset6 J1 | 71.3 | 75.9 | GCCCTCCTGCCGACCTCCTT |
| Jset6 J2 | 71.8 | 76.6 | CCCAGGGATGGCAGCTGGTGT |
| Jset6 J3 | 72.3 | 75.9 | ACATGGCCCAGCGCAGACCAA |
| Jset6 J4 | 70.7 | 74.5 | CGGGGCTCTCTTGGCAGGAGA |
| Jset6 J5 | 70.7 | 74.5 | CCCCAGCTTTCTTTCCTGACCTCCAA |
| Jset6 J6 | 71.0 | 75.9 | GAGGACCAACCTGCAATGCTCAGGAA |
| CLLint J1a | 72.8 | | CCCTTGCCTGGCCCAGTACACCT |
| CLLint J2a | 72.1 | | AGAAGACTGGGAGGGGCTGCAGT |
| CLLint J3a | 71.9 | | CCAGCTCCAGGACAGAGGACGCT |
| CLLint J4a | 70.8 | | CCTTCAGAGTTAAAGCAGGAGAGAGGTTGTGA |
| CLLint J5a | 71.3 | | CGCTGAGTCTCCCTAAGTGGACTCAGAGA |
| CLLint J6 | 72.4 | | GCAGTAGCAGAAAACAAAGGCCCTAGA |
| J1dupa | 72.3 | 75.9 | CCTCCTGCCGACCTCCTTTGCTGA |
| J2dupa | 72.2 | 75.9 | GCCGGCTGCAGACCCCAGA |

-continued

| name | Tm | Tc | primer sequence |
|---|---|---|---|
| J3dupa | 72.2 | 75.9 | GGCCCAGCGCAGACCAAGGA |
| J4dupa | 71.7 | 75.9 | GCCCTTGCCCCTCGTCTGTGT |
| J5dupa | 71.7 | 74.5 | TCCCCAGCTTTCTTTCCTGACCTCCAA |
| J6dupa | 72.0 | 76.6 | AGGAAACCCCACAGGCAGTAGCAGAA |
| setA J1 | 72.6 | 74.5 | CCTCTGCCCTCCTGCTTCTCCCATACA |
| setA J2 | 72.4 | 74.5 | GCTAAGTGACAGCAGGGCTCTGGCAT |
| setA J3 | 71.4 | 74.5 | CGTGGTCCCAAACAGCCGGAGAA |
| setA J4 | 72.1 | 74.5 | CTGTTGCCTCAGGGCATCCTCCTGA |
| setA J5 | 72 | 77 | GAGGACAGGCTGGGTTCCCATTCGAA |
| setA J6 | 71.2 | 75.9 | GCCCAGGTCCCCTCGGAACAT |
| setB J1 | 72.3 | 74.5 | GGCTCCCCGCTATCCCCAGACA |
| setB J2 | 71.9 | 75.9 | GCCTGGTGCCTGGACAGAGAAGACT |
| setB J3 | 72.1 | 76.6 | CTGGGCCCAGAGAAAGGAGGCAGAA |
| setB J4 | 71.9 | 75.9 | CCCTTCAGAGTTAAAGCAGGAGAGAGGTTGTGA |
| setB J5 | 71.5 | 77 | CCCTGGCAAGCTGAGTCTCCCTAAGT |
| setB J6 | 71.7 | 74.5 | GGCAGTAGCAGAAAACAAAGGCCCTAGAGT |

Example 3

Testing of the Primer

1. Determining amplification efficiency, Tc and specificity

One or several primers are synthesised for each patient. Using a gradient of annealing temperatures, each primer is tested for its ability to amplify from leukaemic DNA and for its failure to amplify from nonleukaemic DNA. An example is

| DNA | D 0 | D 0 | D 0 | D 0 | D 0 | D 0 | D 0 | PBL | Tc |
|---|---|---|---|---|---|---|---|---|---|
| temp | 67.0 | 66.7 | 66.2 | 65.2 | 64.0 | 63.0 | 62.4 | 62.0 | |
| Ct | 41.7 | 38.6 | 33.2 | 29.8 | 29.5 | 29.6 | 29.2 | NA | 65.2 |
| Ct | 38.7 | 37.0 | 33.2 | 30.7 | 28.8 | 29.7 | 30.2 | NA | 65.2 |

The top row shows the source of the DNA (day 0 leukaemic, D0, or non-leukaemic peripheral blood lymphocytes, PBL), the next row shows the range of annealing temperatures, and the lowest 2 rows show the Ct values observed with testing 2 different primers. The column on the right shows the Tc values. Both primers amplified efficiently at a temperature of 65.2° C. or below. Neither primer produced amplification (NA) with PBL at 62.0° C. As this temperature is more than 3° below the Tc value the results suggest that it is unlikely that nonspecificity will be observed in future experiments.

2. The selected primer is next tested to ensure that its ability to amplify the rearranged target gene in the leukaemic DNA is not inhibited by the concomitant presence of non-leukaemic DNA.

An example of a test is shown below. The presence of either 500 ng or 1 µg of nonleukaemic DNA made no difference to the CT observed with 400 pg of leukaemic DNA. No amplification was observed with 500 ng of non-leukaemic DNA alone or with the water control

| | |
|---|---|
| Do | 32.89 |
| Do + 500 ng | 32.90 |
| Do + 1 µg | 32.78 |
| 500 ng | N/A |
| water | N/A |

3. Definitive testing for nonspecificity

This can be performed at the end of the primer workup or during the first definitive experiment measuring MRD. The primers are tested against 20 wells, each containing 1 µg of pooled DNA obtained from five non-leukaemic individuals.

Example 4

Sequences of Patient ASO Primers with Tm and Tc Values

V or V, N, D, N, J, show recombining regions targeted by the primer. Primers were for samples from patients with acute lymphoblastic or chronic lymphocytic leukaemia.

| primer sequence | Tm | Tc |
|---|---|---|
| GACTAGCGGTTGGGA | 58.6 | 66.2 |
| GCGAGGGAGATCCAA | 58.7 | 66.7 |

-continued

| primer sequence | Tm | Tc |
|---|---|---|
| GGTGACTGCTCTACGAT | 59.3 | 66.7 |
| CTAACTGGGCGCTGA | 59.4 | 65.2 |
| CCCCTTACTATGATAAGGGGT | 59.5 | 65.2 |
| CAGCTGTCATGGGACT | 59.6 | 65.0 |
| GGTCGGGGGTAGA | 59.7 | 66.2 |
| GGTAGCTGCTACCCTTT | 59.7 | 65.0 |
| CTTAGCAGTGGCACCT | 59.9 | 67.5 |
| TTGGAGTGGTTAAGATACTACTA | 60.0 | 66.2 |
| ATCAGTGGGGGGT | 60.0 | 62.0 |
| CAGGGGGTCCGAGA | 60.1 | 63.2 |
| CCAGCTGCTATTCAAACTTT | 60.5 | 67.2 |
| GGGTTGGGGGGTACT | 61.0 | 66.5 |
| GGCTGGTACCCG CTA | 61.4 | 68.0 |
| GCTCGTCCTGGGTACTA | 61.4 | 67.2 |
| GTAGTGGTGGTAGCTGCTACCCTTTA | 68.2 | 75.0 |
| CTCATGGGCTCGTCCTGGGTACTA | 69.4 | 76.0 |
| TTGGAGTGGTTATTGGGGGCAACCTAT | 70.6 | 73.9 |
| GGATATTGTAGTAGTACCAGCTGTCATGGGACTA | 69.9 | 74.8 |
| CAGCTGTGTATTTTTGTGCTAGTGCTCGATT | 69.9 | 72.0 |
| GGGAGAGATCAGTGGGGGGT | 70.1 | 74.5 |
| GGATATTGTAGTAGTACCAGCTGTCATGGGACT | 70.2 | 74.2 |
| GAGAGACCTAATTAGGGTTGGGGGGTACT | 70.3 | 71.0 |
| CTCGTGTCACTGTGAGGATATTGTAGTAGTACCAGCTGCTATTCAAACTTT | 70.8 | 76.6 |
| CTG TGC TAA CTG GGG AGG GGCT | 70.8 | 75.0 |
| GGCGGGTCGGGGGTAGA | 71.2 | 74.0 |
| GTCACTGTGGTATTACGATTTTTGGAGTGGTTAAGATACTACTA | 71.3 | 74.4 |
| GAGATAGCCCCTTAGCAGTGGCACCT | 71.6 | 76.0 |
| GCAAGACAAGCCCGGTCCGATA | 69.5 | 75.0 |
| GTGATGGCGTGGTGACTGCTCTACGAT | 71.7 | 76.5 |
| CTTAGCGGTGGCGAGGGAGATCCAA | 71.9 | 77.5 |
| GTAACATTGTGGGACAGGGTTGGTGGCTACA | 74.0 | 77.8 |
| GACCCCCTTAAAATAGCAGTGGCTGGTACCCGCTA | 75.1 | 78.5 |
| GTGCCAGCAGCGACTAGCGGTTGGGA | 75.4 | 76.0 |

Example 5

Gradient—For Testing Primers

Each primer is looked at in duplicate at 6 different temperatures.

Normal DNA is run at 2 lower temperatures to check the primers for non-specificity Dilute diagnostic sample to 200 pg/µl. Add 2 µl/tube, need 28 µl/primer set Dilute normal DNA to 250 ng/µl Add D0 DNA to rows A B C D E and F Add PBL DNA to rows G and H Table is for 6 primers but can be decreased to run less primers on a plate or in strips.

|  | 1 | 106 |
|---|---|---|
| H2O | 12.56 | 1331.36 |
| 10X Platinum Buffer | 2 | 212 |
| 50 mM MgCl₂ | 2 | 212 |
| 10 mM dNTP | 0.6 | 63.6 |
| syto 82 1/100 | 0.2 | 21.2 |
| Reverse Primer @ 50 uM | 0.16 | 16.96 |
| Probe IgHJFAM @ 20 uM | 0.16 | 16.96 |
| Platinum taq 5 U/ul | 0.16 | 16.96 |
|  | 17.84 | 1891.04 |

Divide into 6 at 17.25×17.84 µl=307.74 µl and add 2.76 ul forward primer @ 50 uM For each primer set remove 13×18 µl=234 µl and add 26 µl D0 DNA at 200 pg/µl To remainder of mix add 8.5 µl of normal DNA at 250 ng/µl. (500 ng/well)

Aliquot 20 µl of D0 mix into rows ABCDE and F and 20 µl normal DNA mix into rows G and H, seal and run the following protocol.

Run on PCR machine CFX 91° C. 3 mins.×1:
97° C. 15 secs, 68-75° C. 30 secs, ×5 cycles
96° C. 15 secs, 68-75° C. 30 secs, ×5 cycles
94° C. 15 secs, 68-75° C. 30 secs, ×35 cycles
Melt 70° C.-95° C.

This method is for testing the amplification efficiency and specificity of the primers at a range of annealing temperatures.

1 and 106 refer to component volumes for a single well or for the total wells respectively

Example 6

APPENDIX 5

Worksheet 4: To Make up mixes for quantification using single primer

Patient Diagnostic DNA at 1 ng/µl
Pbl DNA need 120 µl at 250 ng/µl 4 ùl/tube

Dilutions in MR tubes

From 1 ng/ul    3 ul + 27 ul FG3  0.1 ng/ul
From 0.1 ng/ul  2 ul + 18 ul FG3  0.01 ng/ul
Need pbl 250 ng/ul to make up mixes to add 20 ul/tube

|  | No. Tubes | pat DNA µl | pblµl | H2Oµl to 20 µl/tube |
|---|---|---|---|---|
| $1 \times 10^3$ | 2.25 | 1 ng | 2.25 | 9 at 250 ng/µl    33.75 |
| $1 \times 10^{-4}$ | 2.25 | 0.1 ng | 2.25 | 9 at 250 ng/µl    33.75 |
| $2 \times 10^{-5}$ | 3.25 | 0.01 ng | 6.5 | 13 at 250 ng/µl   42.25 |
| Pbl | 21 | — | — | 84 at 250 ng/µl   336 |

| Copies/tube | | |
|---|---|---|
| $10^{-3}$ | 1 ng/1 µg | 151 |
| $10^{-4}$ | 0.1 ng/1 µg | 15.1 |
| $2 \times 10^{-5}$ | 0.01 ng/1 µg | 3.00 |

Example 7

Quantification Using Single Primer for 2 Samples, 2 Tubes and 5 Tubes

|  | 1 | 41 |
|---|---|---|
| H2O | 16 | 656 |
| 10X Buffer | 5 | 205 |
| MgCl₂ | 5 | 205 |
| TTP | 1.5 | 61.5 |
| single primer 500 ng | 0.4 | 16.4 |
| syto 82 | 0.5 | 20.5 |
| Reverse 500 ng/µl | 0.4 | 16.4 |
| igHJ probe | 0.4 | 16.4 |
| Platinum taq 5 U/ul | 0.8 | 32.8 |
|  | 30 | 1230 |

| | | |
|---|---|---|
| Mix 1)2)$10^{-3}$ $10^{-4}$ 2 tubes each | 30 ul PCR mix<br>20 ul DNA mix | 1-4 |
| Mix 3) $10^{-5}$ 3.25 tubes | 50 µl<br>97.5 µl PCR Mix<br>65 µl DNA mix | 5-7 |
| Mix 4) Sample 2.2 tubes | 162.5 µl<br>66 µl PCR Mix<br>µl DNA<br>µl water | 8-9 |
| Mix 5) Sample 5.25 tubes | 110 µl<br>157.5 µl PCR Mix<br>µl DNA<br>ul water | 10-14 |
| | 262.5 µl | |
| Mix 6) pbl DNA 21 tubes | 630 µl mix<br>420 µl DNA | 15-34 |
| Mix 7) +ve control X2 tubes | 1050 µl<br>30 ul mix<br>10 ul 0.1 ng/ul D0 in TE<br>10 µl water | 35-36 |
| | 50 ul × 2 | |

| | | |
|---|---|---|
| Mix 8) negative X2 tubes | 30 ul mix 20 ul H₂O | 37-38 |
| | 50 ul × 2 | |
| Run: 91° c. 3 mins | | |
| | 97° C., 15 sec; 72° C., 30 sec × 5 cycles 96° C., 15 sec; 72° C., 30 sec × 5 cycles, 94° C., 15 sec; 72° C., 30 sec × 35 cycles | |

Example 8

Melting Curve Analysis

The PCR contains the fluorescent dye Syto 82 at a concentration of 0.5 µM. Preliminary studies showed that this concentration did not prolong the Ct as measured by a reporter probe. Fluorescence is measured as the temperature is slowly increased and the results analysed using the appropriate program. The first derivative of the fluorescence vs temperature curve shows the peaks for non-specific amplification and specific amplification.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

BIBLIOGRAPHY

Brisco, M. J., Bartley, P. A., and Morley, A. A. Antisense PCR: A simple and robust method for performing nested single-tube PCR. Analytical Biochemistry 2011; 409:176-182

Bruggemann M, van der Velden V H, Raff T, Droese J, Ritgen M, Pott C, et al. Rearranged T-cell receptor beta genes represent powerful targets for quantification of minimal residual disease in childhood and adult T-cell acute lymphoblastic leukemia. Leukemia. 2004; 18(4): 709-19.

Li A-H, Forestier E, Rosenquist R, and Roos G. Minimal residual disease quantification in childhood acute lymphoblastic leukemia by real-time polymerase chain reaction using the SYBR green dye. Experimental Hematology 2002; 30:1170-1177

Morley A A, Latham S, Brisco M J, Sykes P J, Sutton R, Hughes E, et al. Sensitive and specific measurement of minimal residual disease in acute lymphoblastic leukemia. J Mol Diagn. 2009; 11(3):201-10.

Nakao M, Janssen J W, Flohr T, Bartram C R. Rapid and reliable quantification of minimal residual disease in acute lymphoblastic leukemia using rearranged immunoglobulin and T-cell receptor loci by LightCycler technology. Cancer Res. 2000; 60(12):3281-9.

Pongers-Willemse M J, Seriu T, Stolz F, d'Aniello E, Gameiro P, Pisa P, et al. Primers and protocols for standardized detection of minimal residual disease in acute lymphoblastic leukemia using immunoglobulin and T cell receptor gene rearrangements and TAL1 deletions as PCR targets: report of the BIOMED-1 CONCERTED ACTION: investigation of minimal residual disease in acute leukemia. Leukemia. 1999; 13(1):110-8.

van der Velden V H, Boeckx N, van Wering E R, van Dongen J J. Detection of minimal residual disease in acute leukemia. J Biol Regul Homeost Agents. 2004; 18(2): 146-54.

van der Velden V H, Panzer-Grumayer E R, Cazzaniga G, Flohr T, Sutton R, Schrauder A, et al. Optimization of PCR-based minimal residual disease diagnostics for childhood acute lymphoblastic leukemia in a multi-center setting. Leukemia. 2007; 21(4):706-13.

van der Velden V H, van Dongen J J. MRD detection in acute lymphoblastic leukemia patients using Ig/TCR gene rearrangements as targets for real-time quantitative PCR. Methods Mol Biol. 2009; 538:115-50.

van der Velden V H, Wijkhuijs J M, Jacobs D C, van Wering E R, van Dongen J J. T cell receptor gamma gene rearrangements as targets for detection of minimal residual disease in acute lymphoblastic leukemia by real-time quantitative PCR analysis. Leukemia. 2002; 16(7): 1372-80.

van der Velden V H, Willemse M J, van der Schoot C E, Hahlen K, van Wering E R, van Dongen J J. Immunoglobulin kappa deleting element rearrangements in precursor-B acute lymphoblastic leukemia are stable targets for detection of minimal residual disease by real-time quantitative PCR. Leukemia. 2002; 16(5):928-36.

van der Velden V H J, Noordijk R, Brussee M, Hoogeveen P, Homburg C, de Haas V, C. van der Schoot E, van Dongen J J M. Minimal residual disease diagnostics in acute lymphoblastic leukaemia: Impact of primer characteristics and size of junctional regions. British Journal of Haematology, 2014, 164, 451-464

Verhagen O J, Willemse M J, Breunis W B, Wijkhuijs A J, Jacobs D C, Joosten S A, et al. Application of germline IGH probes in real-time quantitative PCR for the detection of minimal residual disease in acute lymphoblastic leukemia. Leukemia. 2000; 14(8):1426-35.

The invention claimed is:

1. A method of amplifying an Ig or TCR nucleic acid region which is characterised by the rearrangement of two or more V, D or J gene segments said method comprising contacting a nucleic acid sample of interest with forward and reverse primers directed to said rearranged Ig or TCR nucleic acid region and amplifying said nucleic acid sample using an annealing temperature within the range between Tc and (Tc-3° C.) of the subject amplification reaction, and optionally:
   (i) at least one primer which comprises at least one A and/or T nucleotide at the 3' terminal nucleotide position; and/or
   (ii) conducting a melting curve analysis.

2. A method of detecting and/or monitoring a clonal population of cells in a mammal, which clonal cells are characterised by an Ig or TCR nucleic acid region which is characterised by the rearrangement of two or more V, D or J gene segments, said method comprising:
   (i) contacting DNA from a biological sample derived from a mammal with forward and reverse primers directed to said rearranged Ig or TCR nucleic acid region under conditions sufficient to facilitate interaction of said primers with said nucleic acid region;
   (ii) amplifying said nucleic acid region using an annealing temperature within the range between Tc and (Tc-3° C.) of the subject amplification reaction, and optionally (a) at least one primer which comprises at least one A and/or T nucleotide at the 3' terminal nucleotide position of said primer; and/or (b) a means to conduct a melting curve analysis; and
   (iii) detecting the product amplified in accordance with step (ii).

3. The method according to claim 1 wherein said method comprises using both an annealing temperature within the range between Tc and (Tc-3° C.) of the subject amplification reaction and one or more primers which comprise an A or T nucleotide at the 3' terminal nucleotide position of said primer.

4. The method according to claim 1 wherein said nucleic acid region is DNA.

5. The method according to claim 1 wherein there is an A and/or T nucleotide at each of the two, three, four, five or six most 3' terminal nucleotide positions of said primer.

6. The method according to claim 1 wherein either or both of the forward or reverse primers are designed to include said A and/or T nucleotides.

7. The method according to claim 1 wherein only said reverse primer is designed to include said A and/or T nucleotides.

8. The method according to claim 1 wherein said VDJ rearrangement is a partial rearrangement and there is an N region situated at the junction between one or more of the rearranged V and D gene segments, the rearranged D and J gene segments or the rearranged V and J gene segments.

9. The method according to claim 1 wherein said VDJ rearrangement is a complete rearrangement and there is an N region situated at the junction between one or more of the rearranged V and D gene segments, the rearranged D and J gene segments or the rearranged V and J gene segments.

10. The method according to claim 1 wherein said VDJ rearrangement is a partial rearrangement and there is an N region situated within one or more of the V gene segment, D gene segment or J gene segment.

11. The method according to claim 1 wherein said VDJ rearrangement is a complete rearrangement and there is an N region situated within one or more of the V gene segment, D gene segment or J gene segment.

12. The method according to claim 1 wherein at least one of said primers comprises a hybridisation subregion directed to one N gene segment of the rearranged V, D and J gene segments.

13. The method according to claim 1 wherein at least one of said primers comprises hybridisation subregions directed to at least two N gene segments of the rearranged V, D and J gene segments.

14. The method according to claim 1 wherein the primer directed to the J gene segment comprises at least one A and/or T nucleotide at its 3' end.

15. The method according to claim 1 wherein a primer subregion is modified to substitute one or more of the nucleotides of said subregion with a nucleotide from an N mixture.

16. The method according to claim 15 wherein every fourth nucleotide of said subregion is substituted.

17. The method according to claim 16 wherein a sequence of 3-7 adjacent nucleotides of said subregion are substituted.

18. The method according to claim 1 wherein a melting curve analysis is performed.

19. The method according to claim 18 wherein said melting curve analysis is performed using a dye.

20. The method according to claim 19 wherein said dye is a fluorophore.

21. The method according to claim 1 wherein said method includes a Ct determination step.

22. The method according to claim 21 wherein said Ct determination is performed using a probe directed to said rearranged Ig or TCR region and which probe is coupled to a detection means.

23. The method according to claim 22 wherein said detection means is a fluorescent molecule.

24. The method according to claim 1 wherein said at least one primer is an ASO primer.

25. The method according to claim 1 wherein said reverse primer is directed to a J segment.

26. The method according to claim 1 wherein said amplification is polymerase chain reaction.

27. The method according to claim 2 wherein said clonal cells are neoplastic cells.

28. The method according to claim 27 wherein said neoplastic cells are lymphoid neoplastic cells.

29. The method according to claim 28 wherein said lymphoid neoplastic cells are malignant.

30. The method according to claim 29 wherein said lymphoid malignant cells are indicative of lymphoid leukaemia, acute lymphoblastic leukaemia, chronic lymphocytic leukaemia or myeloma.

31. The method according to claim 2 wherein said method is used to detect minimum residual disease.

32. The method according to claim 31 wherein said minimum residual disease is detected in the context of lymphoid leukaemia.

\* \* \* \* \*

UNITED STATES PATENT AND TRADEMARK OFFICE
CERTIFICATE OF CORRECTION

PATENT NO. : 11,306,352 B2
APPLICATION NO. : 16/478786
DATED : April 19, 2022
INVENTOR(S) : Alexander Alan Morley It is certified that error appears in the above-identified patent and that said Letters Patent is hereby corrected as shown below:

In the Specification

Column 1, Line 61, delete "that that" and insert -- that --.

Column 4, Line 50, delete "bases" and insert -- bases. --.

Column 4, Line 67, delete "2000)" and insert -- 2000). --.

Column 5, Line 7, delete "primer" and insert -- primer. --.

Column 8, Line 43, delete "target" and insert -- target. --.

Column 16, Line 14-15, delete "of of" and insert -- of --.

Column 17, Line 41, (approx.), delete "FIG. 4" and insert -- FIG. 4. --.

Column 29, Line 44, (approx.), delete "D 0" and insert -- D0 --.

Column 29, Line 44, (approx.), delete "D 0" and insert -- D0 --.

Column 29, Line 44, (approx.), delete "D 0" and insert -- D0 --.

Column 29, Line 44, (approx.), delete "D 0" and insert -- D0 --.

Column 29, Line 44, (approx.), delete "D 0" and insert -- D0 --.

Column 29, Line 44, (approx.), delete "D 0" and insert -- D0 --.

Column 29, Line 44, (approx.), delete "D 0" and insert -- D0 --.

Signed and Sealed this
Twenty-eighth Day of February, 2023

Katherine Kelly Vidal
*Director of the United States Patent and Trademark Office*

Column 30, Line 39, (approx.), delete "control" and insert -- control. --.

Column 33, Line 22, delete "91°C." and insert -- 91° C. --.

Column 33, Line 31, delete "respectively" and insert -- respectively. --.

Column 35, Line 38, (approx.), delete "182" and insert -- 182. --.

Column 35, Line 50, (approx.), delete "1177" and insert -- 1177. --.

Column 36, Line 47, delete "464" and insert -- 464. --.